US009561362B2

(12) United States Patent
Malinowski

(10) Patent No.: US 9,561,362 B2
(45) Date of Patent: Feb. 7, 2017

(54) SYSTEMS AND METHODS FOR MAKING AND USING IMPROVED CONTACT ARRAYS FOR ELECTRICAL STIMULATION SYSTEMS

(71) Applicant: Boston Scientific Neuromodulation Corporation, Valencia, CA (US)

(72) Inventor: Zdzislaw Bernard Malinowski, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/935,271

(22) Filed: Nov. 6, 2015

(65) Prior Publication Data

US 2016/0129242 A1    May 12, 2016

Related U.S. Application Data

(60) Provisional application No. 62/077,784, filed on Nov. 10, 2014.

(51) Int. Cl.
*A61N 1/05* (2006.01)
*H01R 43/26* (2006.01)

(52) U.S. Cl.
CPC .............. *A61N 1/0551* (2013.01); *A61N 1/05* (2013.01); *H01R 43/26* (2013.01)

(58) Field of Classification Search
CPC ........ A61N 1/0551; A61N 1/05; A61N 1/048; A61N 1/3752; A61N 1/3754; H01R 43/24
See application file for complete search history.

(56) References Cited

U.S. PATENT DOCUMENTS

| | | |
|---|---|---|
| 4,602,624 A | 7/1986 | Naples et al. |
| 4,630,611 A | 12/1986 | King |
| 4,744,370 A | 5/1988 | Harris |
| 5,000,194 A | 3/1991 | van den Honert et al. |
| 5,135,001 A | 8/1992 | Sinofsky et al. |
| 5,374,285 A | 12/1994 | Vaiani et al. |
| 5,458,629 A | 10/1995 | Baudino et al. |

(Continued)

FOREIGN PATENT DOCUMENTS

| | | |
|---|---|---|
| EP | 0580928 A1 | 2/1994 |
| EP | 0650694 B1 | 7/1998 |

(Continued)

*Primary Examiner* — Paula J Stice
(74) *Attorney, Agent, or Firm* — Lowe Graham Jones PLLC; Bruce E. Black

(57) ABSTRACT

A segmented-contact set of a lead includes segmented contacts extending around less than an entire circumference of the lead and not in electrical contact with one another. The segmented-contact set includes first and second segmented contacts that each include a stimulation portion and a retention member. The stimulation portion has a stimulation surface exposed along an outer surface of the lead. The retention member is coupled to the stimulation portion. The stimulation portion and the retention member collectively form a loop of material that extends around a center transverse axis of the lead beneath the outer surface. A first insulating member is disposed between the stimulation portion of the first segmented contact and the retention member of the second segmented contact. A second insulating member is disposed between the stimulation portion of the second segmented contact and the retention member of the first segmented contact.

20 Claims, 21 Drawing Sheets

(56) References Cited

U.S. PATENT DOCUMENTS

| | | |
|---|---|---|
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,181,969 B1 | 1/2001 | Gord |
| 6,322,559 B1 | 11/2001 | Daulton et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,609,029 B1 | 8/2003 | Mann et al. |
| 6,609,032 B1 | 8/2003 | Woods et al. |
| 6,678,564 B2 | 1/2004 | Ketterl et al. |
| 6,741,892 B1 | 5/2004 | Meadows et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,203,548 B2 | 4/2007 | Whitehurst et al. |
| 7,244,150 B1 | 7/2007 | Brase et al. |
| 7,292,890 B2 | 11/2007 | Whitehurst et al. |
| 7,437,193 B2 | 10/2008 | Parramon et al. |
| 7,450,997 B1 | 11/2008 | Pianca et al. |
| 7,489,971 B1 | 2/2009 | Franz |
| 7,668,601 B2 | 2/2010 | Hegland et al. |
| 7,672,734 B2 | 3/2010 | Anderson et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,809,446 B2 | 10/2010 | Meadows |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,175,710 B2 | 5/2012 | He |
| 8,224,450 B2 | 7/2012 | Brase |
| 8,225,504 B2 | 7/2012 | Dye et al. |
| 8,271,094 B1 | 9/2012 | Moffitt et al. |
| 8,295,944 B2 | 10/2012 | Howard et al. |
| 8,321,025 B2 | 11/2012 | Bedenbaugh |
| 8,359,107 B2 | 1/2013 | Pianca et al. |
| 8,364,278 B2 | 1/2013 | Pianca et al. |
| 8,391,985 B2 | 3/2013 | McDonald |
| 8,504,171 B2 | 8/2013 | Ayanoor-Vitikkate et al. |
| 8,583,237 B2 | 11/2013 | Bedenbaugh |
| 8,688,235 B1 | 4/2014 | Pianca et al. |
| 2001/0023368 A1 | 9/2001 | Black et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0150036 A1 | 6/2007 | Anderson |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0276021 A1 | 11/2009 | Meadows et al. |
| 2010/0030298 A1 | 2/2010 | Martens et al. |
| 2010/0036468 A1 | 2/2010 | Decre et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0105071 A1 | 5/2013 | DiGiore et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0151113 A1 | 6/2015 | Govea et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 0158520 A1 | 8/2001 |
| WO | 02068042 A1 | 9/2002 |
| WO | 2004045707 A1 | 6/2004 |
| WO | 2008018067 A2 | 2/2008 |
| WO | 2008053789 A1 | 5/2008 |

(56) References Cited

FOREIGN PATENT DOCUMENTS

| WO | 2008100841 | | 8/2008 |
|---|---|---|---|
| WO | 2009025816 | A1 | 2/2009 |
| WO | 2009102536 | A1 | 8/2009 |
| WO | 2013162775 | A2 | 10/2013 |
| WO | 2014018092 | A1 | 1/2014 |

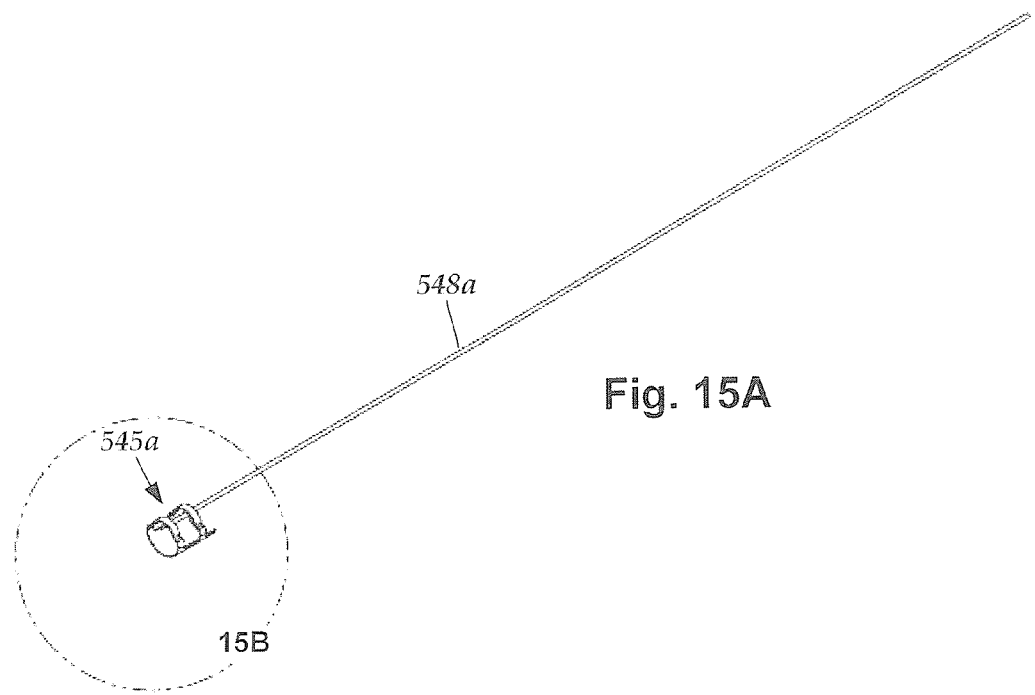
Fig. 15A
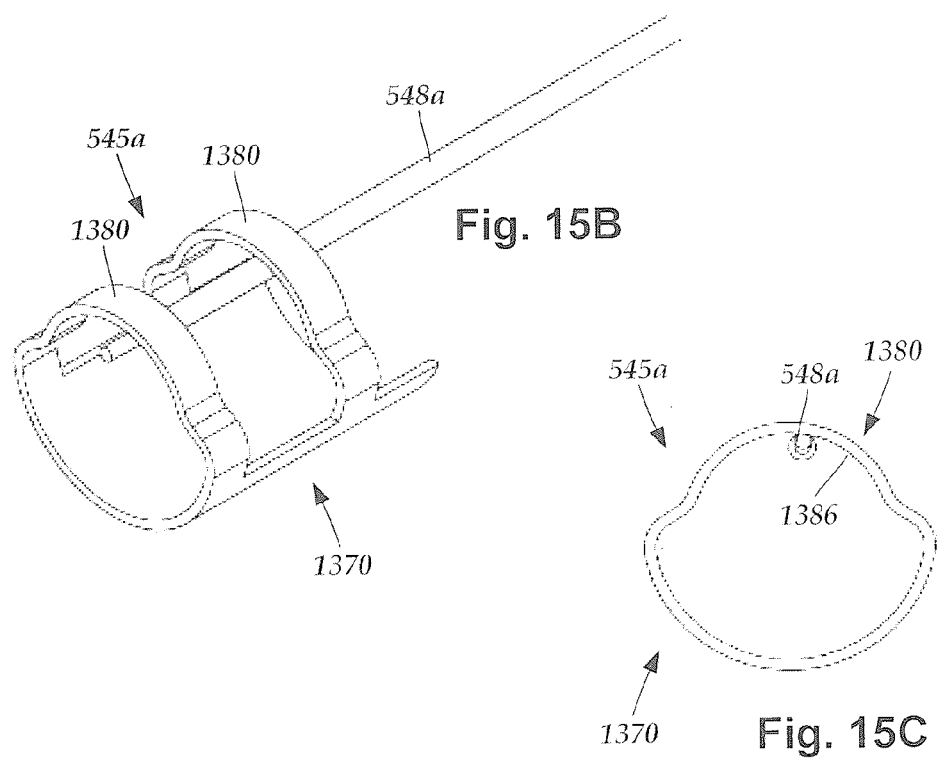
Fig. 15B
Fig. 15C

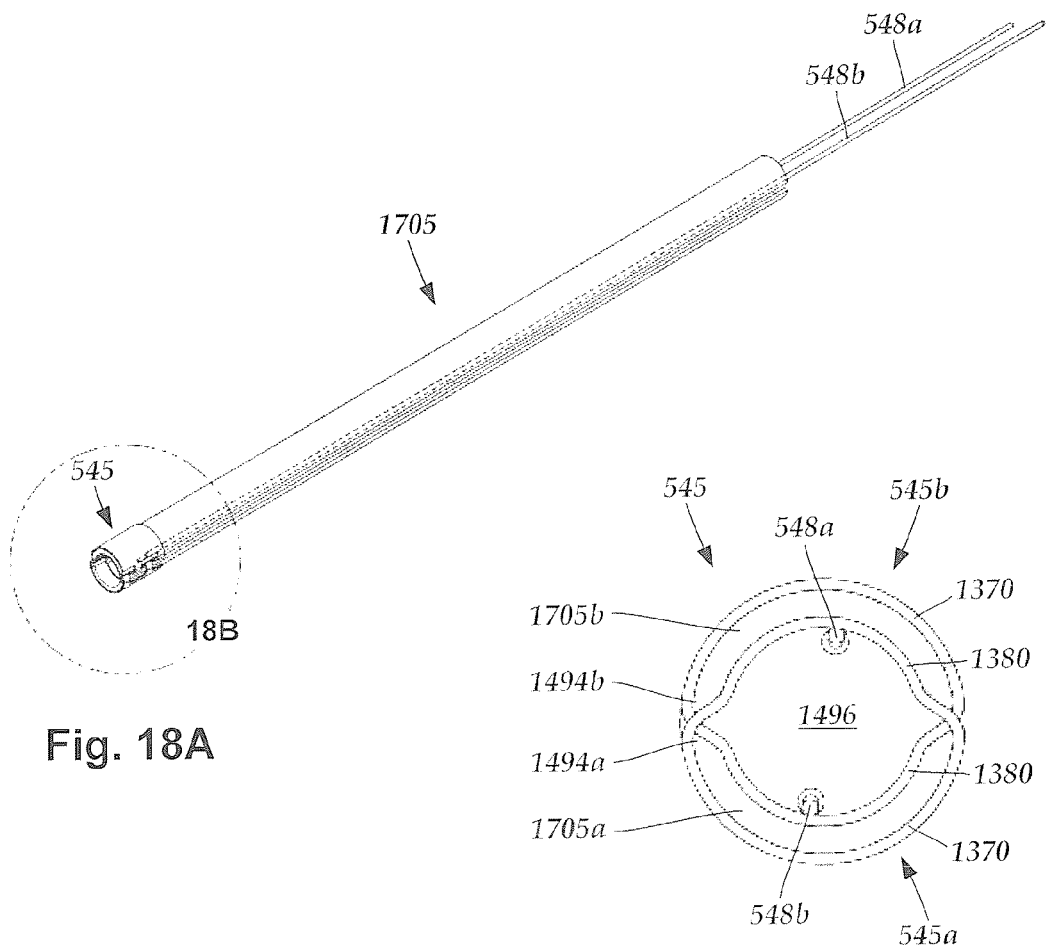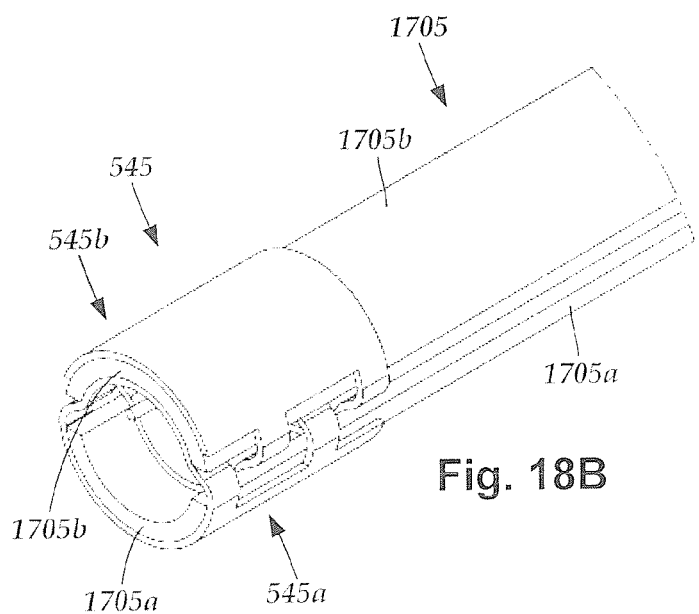
Fig. 18A
Fig. 18C
Fig. 18B

SYSTEMS AND METHODS FOR MAKING AND USING IMPROVED CONTACT ARRAYS FOR ELECTRICAL STIMULATION SYSTEMS

CROSS-REFERENCE TO RELATED APPLICATIONS

This application claims the benefit under 35 U.S.C. §119(e) of U.S. Provisional Patent Application Ser. No. 62/077,784, filed Nov. 10, 2014, which is incorporated herein by reference.

FIELD

The present invention is directed to the area of implantable electrical stimulation systems and methods of making and using the systems. The present invention is also directed to implantable electrical stimulation systems having elongated members with improved contact arrays, as well as methods of making and using the elongated devices, contact arrays, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, an electrical stimulation lead includes a lead body with a proximal portion, at least one distal portion, an outer surface, a circumference, and a longitudinal length. Contacts are disposed along the lead body. The contacts include electrodes disposed along the distal portion of the lead body and terminals disposed along the proximal portion of the lead body. At least one segmented-contact set is formed from at least some of the contacts. The at least one segmented-contact set includes segmented contacts that are each at least partially disposed along a particular longitudinal position of the lead and that each extend around less than the entire circumference of the lead and that are not in electrical contact with one another. Each of the segmented-contact sets includes a first segmented contact and a second segmented contact. The first segmented contact and the second segmented contact each include a stimulation portion and at least one retention member. The stimulation portion has a stimulation surface exposed along the outer surface of the lead body. The at least one retention member is coupled to the stimulation portion and is disposed beneath the outer surface of the lead body. The stimulation portion and the at least one retention member collectively form a loop of material that extends around a center transverse axis of the lead body. A first insulating member is disposed between the stimulation portion of the first segmented contact and the at least one retention member of the second segmented contact. A second insulating member is disposed between the stimulation portion of the second segmented contact and the at least one retention member of the first segmented contact. Lead conductors electrically couple the electrodes to the terminals.

In at least some embodiments, for at least one of the at least one segmented-contact sets, the loop includes a first arced portion having a first curvature and a second arced portion having a second curvature that has a different than the first curvature. In at least some embodiments, the first arced portion is formed along the stimulation portion and the second arced portion is formed along the at least one retention member. In at least some embodiments, the at least one retention member includes at least one transition region having a third arced portion that has a different curvature than at least one of the first arced portion or the second arced portion.

In at least some embodiments, the at least one segmented-contact set includes exactly two segmented contacts.

In at least some embodiments, the at least one segmented-contact set is formed entirely from electrodes of the plurality of electrodes. In at least some embodiments, the at least one segmented-contact set is formed entirely from terminals of the plurality of terminals. In at least some embodiments, the at least one segmented-contact set includes a first segmented-contact set and a second segmented-contact set, where the first segmented-contact set is formed entirely from electrodes of the plurality of electrodes, and where the second segmented-contact set is formed entirely from terminals of the plurality of terminals.

In at least some embodiments, the at least one segmented-contact set includes a plurality of segmented-contact sets, the plurality of segmented-contact sets each formed entirely from terminals of the plurality of terminals.

In at least some embodiments, the at least one segmented-contact set includes a plurality of segmented-contact sets, where each the first insulating member and the second insulating member extend beneath each of the plurality of segmented-contact sets.

In at least some embodiments, the electrical stimulation lead includes a single proximal portion and a plurality of distal portions, the plurality of distal portions including a first distal portion and a second distal portion, and where the plurality of electrodes includes a first electrode array disposed along the first distal portion and a second electrode array disposed along the second distal portion. In at least some embodiments, the at least one segmented-contact set includes a first segmented-contact set, a second segmented-contact set, and a third segmented-contact set, where the first segmented-contact set is formed entirely from electrodes of the first electrode array, where the second segmented-contact set is formed entirely from electrodes of the second electrode array, and where the third segmented-contact set is formed entirely from terminals of the plurality of terminals.

In another embodiment, an electrical stimulation system includes the above-described electrical stimulation lead, a control module, and a connector for receiving the electrical stimulation lead. The control module is electrically coupleable to the plurality of electrodes of the electrical stimulation lead. The control module includes a housing and an electronic subassembly disposed in the housing. The connector includes a connector housing defining a port configured and arranged for receiving the proximal portion of the electrical stimulation lead, and a plurality of connector contacts disposed in the connector housing. The plurality of connector contacts is configured and arranged to couple to the plurality of terminals of the electrical stimulation lead when the proximal portion of the electrical stimulation lead is received by the port.

In at least some embodiments, the plurality of connector contacts includes a plurality of segmented connector contacts, and the electrical stimulation system further includes an alignment assembly configured and arranged for aligning the first and second segmented contacts of the at least one segmented-contact sets circumferentially with the plurality of segmented connector contacts.

In yet another embodiment, a method of forming the above-described electrical stimulation lead includes attaching a first conductor of the plurality of lead conductors to the first segmented contact of the at least one segmented-contact set. A second conductor of the plurality of lead conductors is attached to the second segmented contact of the at least one segmented-contact set. The first segmented contact and the second segmented contact are arranged into the first segmented-contact set with the stimulation portion of the first segmented contact disposed opposite the stimulation portion of the second segmented contact with the at least one retention member of the first segmented contact facing the at least one retention member of the second segmented contact to form a first retention space defined between the stimulation portion of the first segmented contact and the at least one retention member of the second segmented contact and a second retention space defined between the stimulation portion of the second segmented contact and the at least one retention member of the first segmented contact. The first insulating member is extended through the first retention space of the first segmented-contact set. The second insulating member is extended through the second retention space of the first segmented-contact set. The first conductor is attached to a first electrode of the plurality of electrodes disposed along the distal portion of the lead body or a first terminal of the plurality of terminals disposed along the proximal portion of the lead body. The second conductor is attached to one of a second electrode of the plurality of electrodes disposed along the distal portion of the lead body or a second terminal of the plurality of terminals disposed along the proximal portion of the lead body.

In at least some embodiments, arranging the first segmented contact and the second segmented contact into the first segmented-contact set includes arranging a first segmented terminal of the plurality of terminals and a second segmented terminal of the plurality of terminals into a first segmented-terminal set along the proximal portion of the lead.

In at least some embodiments, the above-described method further includes arranging a third segmented terminal of the plurality of terminals and a fourth segmented terminal of the plurality of terminals into a second segmented-terminal set disposed along the proximal portion of the lead and longitudinally displaced from the first segmented-terminal set. In at least some embodiments, the above-described method further includes extending the first insulating member through a third retention space defined along the second segmented-contact set. In at least some embodiments, the above-described method further includes extending the second insulating member through a fourth retention space defined along the second segmented-contact set.

In at least some embodiments, arranging the first segmented contact and the second segmented contact into the first segmented-contact set includes arranging a first segmented electrode of the plurality of electrodes and a second segmented electrode of the plurality of electrodes into a first segmented-electrode set disposed along the at least one distal portion of the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 15A is a schematic perspective view of one embodiment of a conductor coupled to the segmented terminal of FIGS. 13A-13C, according to the invention;

FIG. 15B is a schematic close-up perspective view of one embodiment of the conductor and segmented terminal of FIG. 15A, according to the invention;

FIG. 15C is a schematic end view of one embodiment of one embodiment of the conductor and segmented terminal of FIG. 15A, according to the invention;

FIG. 18A is a schematic perspective view of one embodiment of the insulation of FIGS. 17A-17C disposed between individual segmented terminals of the segmented-terminal set of FIGS. 16A-16C, according to the invention;

FIG. 18B is a schematic close-up perspective view of one embodiment of the insulation of FIGS. 17A-17C disposed between individual segmented terminals of the segmented-terminal set of FIGS. 16A-16C, according to the invention;

FIG. 18C is a schematic end view of one embodiment of the insulation of FIGS. 17A-17C disposed between individual segmented terminals of the segmented-terminal set of FIGS. 16A-16C, according to the invention;

DETAILED DESCRIPTION

The present invention is directed to the area of implantable electrical stimulation systems and methods of making and using the systems. The present invention is also directed to implantable electrical stimulation systems having elongated members with improved contact arrays, as well as methods of making and using the elongated devices, contact arrays, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference.

Figure 1:
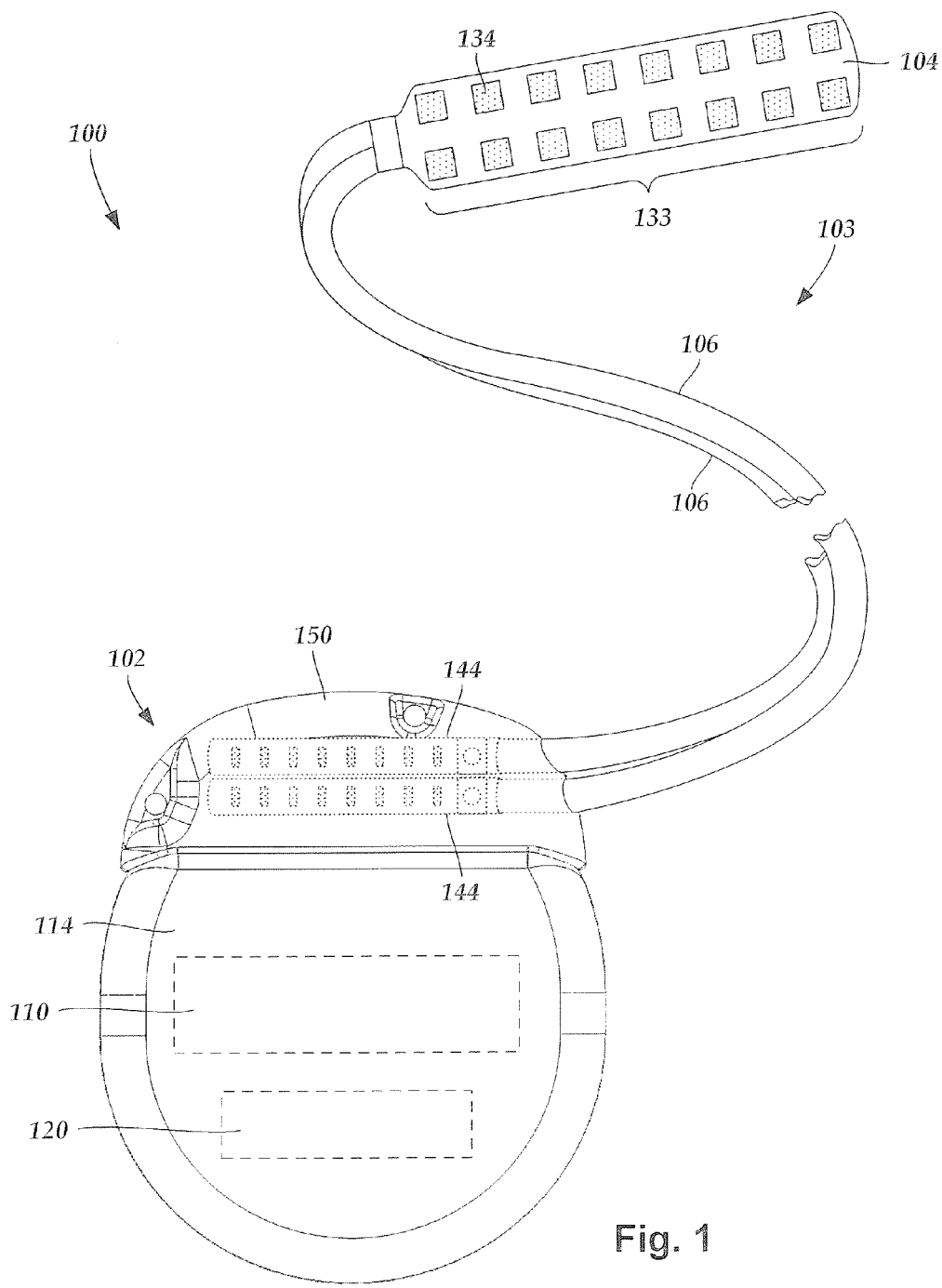
FIG. 1 is a schematic view of one embodiment of an implantable medical device that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connectors 144 into which the proximal end of the one or more lead bodies 106 can be plugged to make an electrical connection via connector contacts (e.g., 316 in FIG. 3A) disposed in the connector 144 and terminals (e.g., 310 in FIG. 3A) on each of the one or more lead bodies 106. The connector contacts are coupled to the electronic subassembly 110 and the terminals are coupled to the electrodes 134. In FIG. 1, two connectors 144 are shown.

The one or more connectors 144 may be disposed in a header 150. The header 150 provides a protective covering over the one or more connectors 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
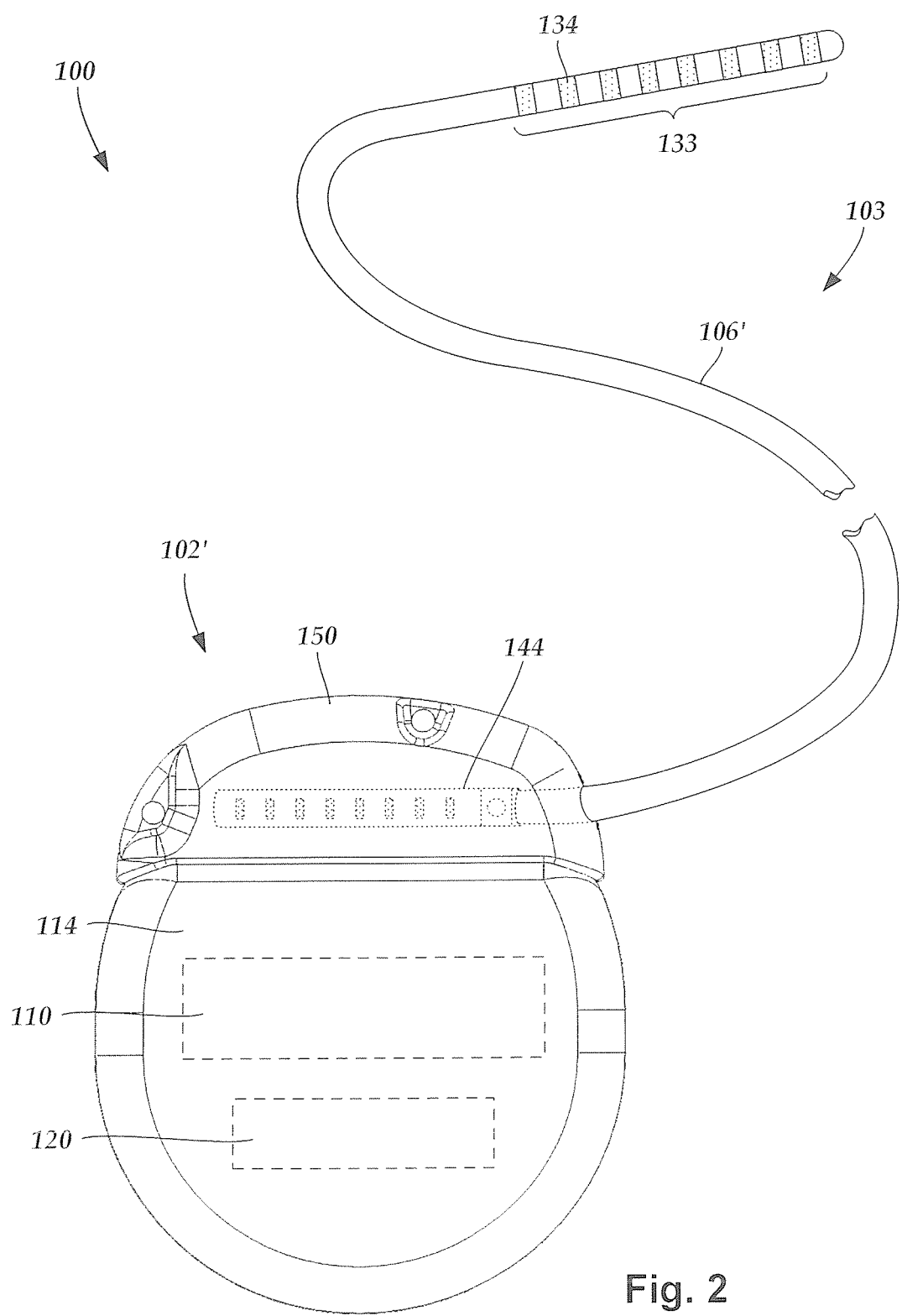
FIG. 2 is a schematic view of another embodiment of an implantable medical device that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connectors (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not show n) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connectors 144 disposed on the control module 102. The control module 102 can include any suitable number of connectors 144 including, for example, two three, four, five, six, seven, eight, or more connectors 144. It will be understood that other numbers of connectors 144 may be used instead. In FIG. 1, each of the two lead bodies 106 includes eight terminals that are shown coupled with eight conductive contacts disposed in a different one of two different connectors 144.

Figure 3A:
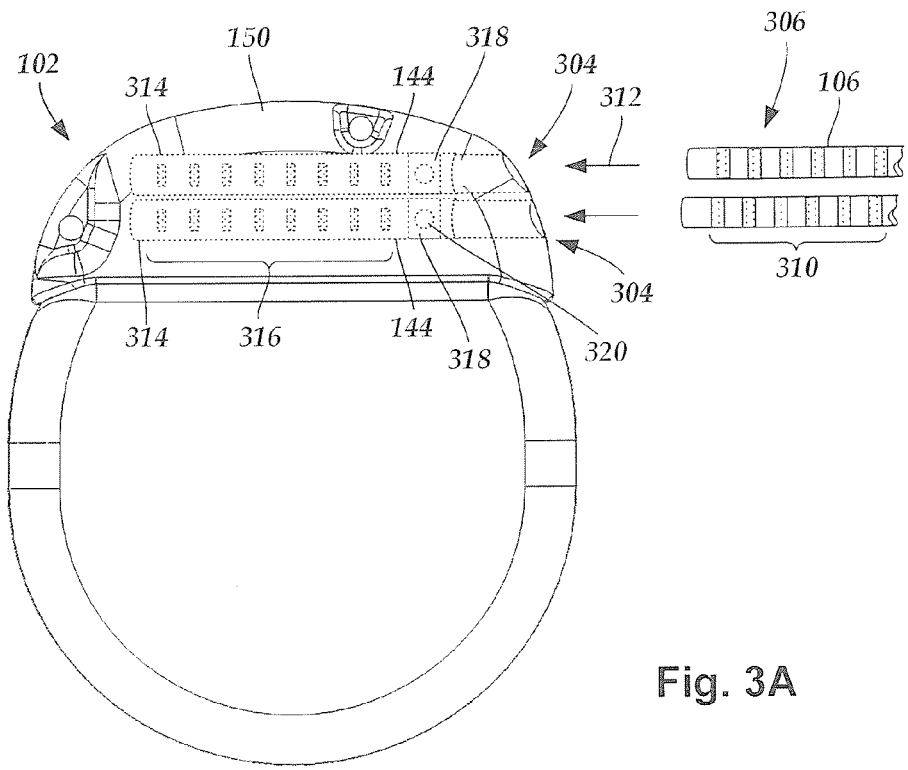
FIG. 3A is a schematic view of one embodiment of a plurality of connectors disposed in the control module of FIG. 1, the connectors configured and arranged to receive the proximal portions of the lead bodies of FIG. 1, according to the invention.
Figure 3B:
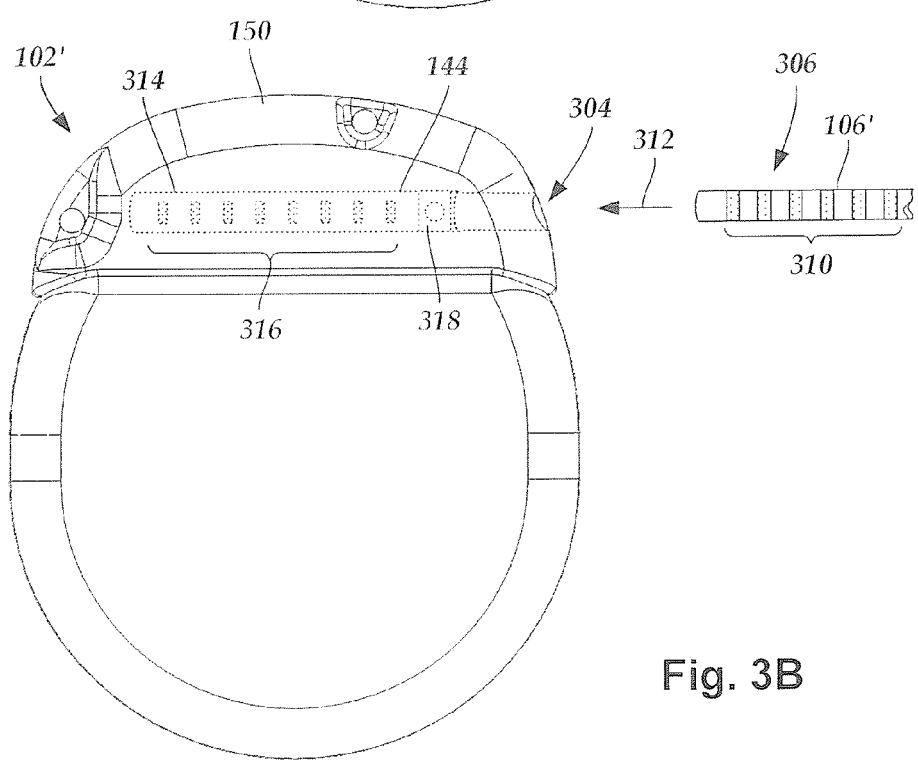
FIG. 3B is a schematic view of one embodiment of a connector disposed in the control module of FIG. 2, the connector configured and arranged to receive the proximal portion of one of the lead body of FIG. 2, according to the invention.

FIG. 3A is a schematic side view of one embodiment of a plurality of connectors 144 disposed on the control module 102. In at least some embodiments, the control module 102 includes two connectors 144. In at least some embodiments, the control module 102 includes four connectors 144. In FIG. 3A, proximal ends 306 of the plurality of lead bodies 106 are shown configured and arranged for insertion to the control module 102. FIG. 3B is a schematic side view of one embodiment of a single connector 144 disposed on the control module 102'. In FIG. 3B, the proximal end 306 of the single lead body 106' is shown configured and arranged for insertion to the control module 102'.

In FIGS. 3A and 3B, the one or more connectors 144 are disposed in the header 150. In at least some embodiments, the header 150 defines one or more lumens 304 into which the proximal end(s) 306 of the one or more lead bodies 106/106' with terminals 310 can be inserted, as shown by directional arrows 312, in order to gain access to the connector contacts disposed in the one or more connectors 144.

The one or more connectors 144 each include a connector housing 314 and a plurality of connector contacts 316 disposed therein. Typically, the connector housing 314 provides access to the plurality of connector contacts 316 via the lumen 304. In at least some embodiments, one or more of the connectors 144 further includes a retaining element 318 configured and arranged to fasten the corresponding lead body 106/106' to the connector 144 when the lead body 106/106' is inserted into the connector 144 to prevent undesired detachment of the lead body 106/106' from the connector 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more lumens 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connectors in control modules are found in, for example, U.S. Pat. Nos. 7,244,150 and 8,224,450, which are incorporated by reference.

Figure 3C:
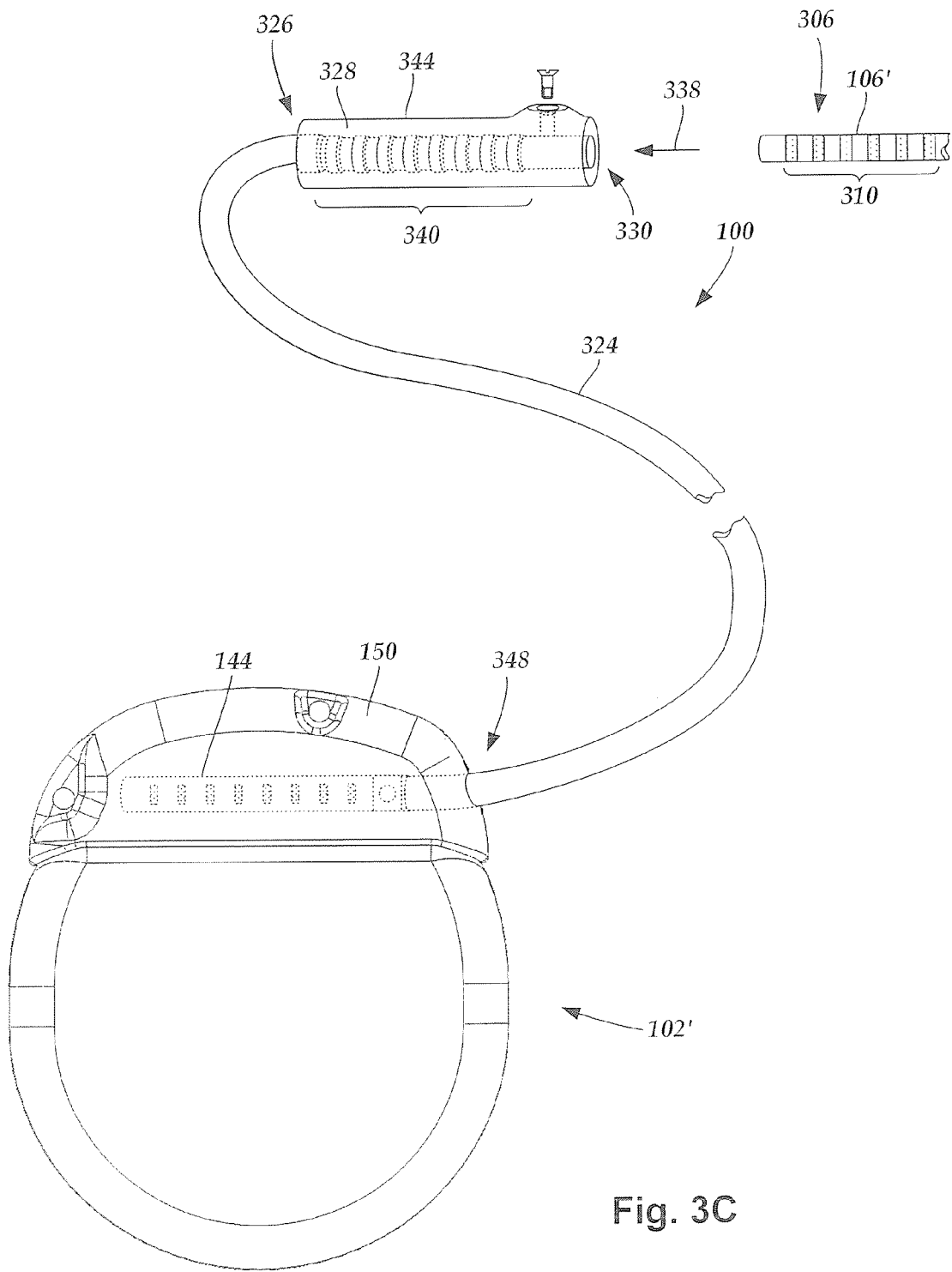
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector 322 is disposed on a lead extension 324. The lead extension connector 322 is shown disposed at a distal end 326 of the lead extension 324. The lead extension connector 322 includes a connector housing 344. The connector housing 344 defines at least one lumen 330 into which a proximal end 306 of the lead body 106' with terminals 310 can be inserted, as shown by directional arrow 338. The lead extension connector 322 also includes a plurality of connector contacts 340. When the lead body 106' is inserted into the lumen 330, the connector contacts 340 disposed in the connector housing 344 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector disposed in another lead extension. In other embodiments (as shown in FIG. 3C), the proximal end 348 of the lead extension 324 is configured and arranged for insertion into the connector 144 disposed on the control module 102'.

It will be understood that the control modules 102/102' can receive either lead bodies 106/106' or lead extensions 324. It will also be understood that the electrical stimulation system 100 can include a plurality of lead extensions 324. For example, each of the lead bodies 106 shown in FIGS. 1 and 3A can, alternatively, be coupled to a different lead extension 324 which, in turn, are each coupled to different ports of a two-port control module, such as the control module 102 of FIGS. 1 and 3A.

Figure 4:
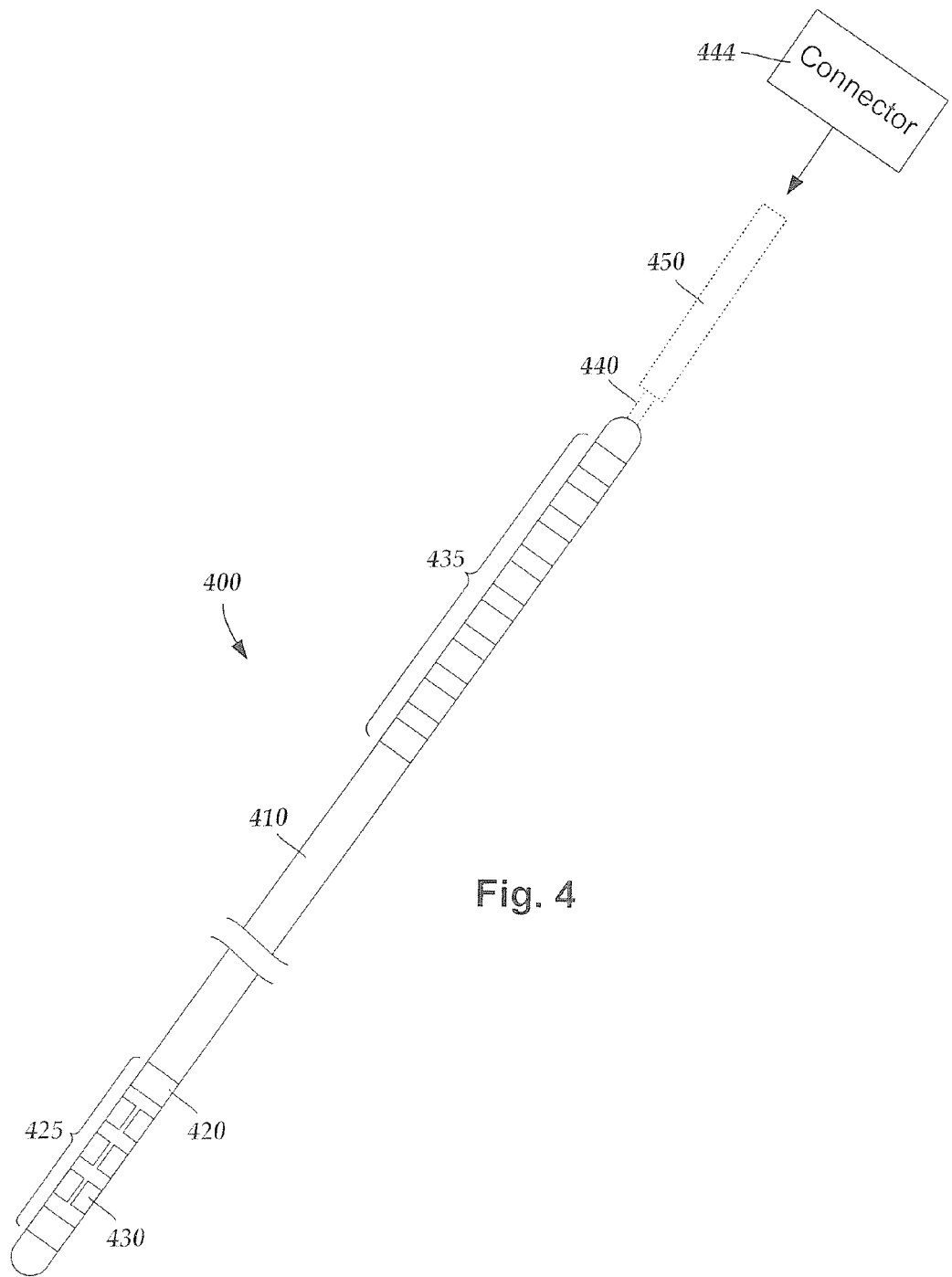
FIG. 4 is a schematic side view of yet another embodiment of an implantable medical device for brain stimulation, according to the invention.

Turning to FIG. 4, in the case of deep brain stimulation, the lead may include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes circumferentially distributed about the lead at a particular longitudinal position.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

FIG. 4 illustrates one embodiment of a device 400 for brain stimulation. The device includes a lead 410, a plurality of electrodes 425 disposed at least partially about a circumference of the lead 410, a plurality of terminals 435, a connector 444 for connection of the electrodes to a control unit, and a stylet 440 for assisting in insertion and positioning of the lead in the patient's brain. The stylet 440 can be made of a rigid material. Examples of suitable materials for the stylet include, but are not limited to, tungsten, stainless steel, and plastic. The stylet 440 may have a handle 450 to assist insertion into the lead 410, as well as rotation of the stylet 440 and lead 410. The connector 444 fits over a proximal end of the lead 410, preferably after removal of the stylet 440.

In FIG. 4, the electrodes 425 are shown as including both ring electrodes, such as ring electrode 420, and segmented electrodes, such as segmented electrodes 430. In some embodiments, the electrodes 425 are all segmented. In other embodiments, the electrodes 425 are all ring-shaped. In FIG. 4, each of the terminals 435 is shown as being ring-shaped. The segmented electrodes of FIG. 4 are shown in sets of two, where the two segmented electrodes of a particular set are electrically isolated from one another and are circumferentially-offset along the lead 410. Any suitable number of segmented electrodes can be formed into a set including, for example, two, three, four, or more segmented electrodes.

Segmented electrodes can be used to direct stimulus current to one side, or even a portion of one side, of the lead. When segmented electrodes are used in conjunction with an implantable pulse generator that delivers current stimulus, current steering can be achieved to more precisely deliver the stimulus to a position around an axis of the lead (i.e., radial positioning around the axis of the lead). Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,295,944; and 8,391,985; and U.S. Patent Applications Publication Nos. 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated herein by reference.

Turning to FIG. 5, in at least some embodiments it may be advantageous to design an elongated member (e.g., a lead, lead extension, splitter, adaptor, or the like) with segmented terminals in addition to, or in lieu of, having segmented electrodes. Such a design may reduce the physical size of the terminal array from conventional terminal arrays with ring-shaped terminals. Consequently, the portion of the elongated member that is inserted into a connector to make electrical contact with the pulse generator can be reduced, as compared to conventional electrical stimulation systems. Alternately, the number of terminals that can be disposed along a proximal portion of an elongated member and that can be inserted into a conventionally-sized connector may be increased from conventional electrical stimulation systems.

As herein described, an array of segmented contacts is disposed along an elongated member (e.g., a lead, lead extension, splitter, adaptor, or the like). The segmented contacts can be terminals, or electrodes, or both. The segmented contacts can be disposed along the proximal portion of the elongated member, the distal portion of the elongated member, an intermediate portion of the elongated member, or some combination thereof.

Segmented contacts (e.g., the segmented electrodes 430 of FIG. 4) are typically formed in sets of two or more contacts, where each of the segmented contacts extends around less than an entire circumference of the elongated member, and where the segmented contacts are not in electrical contact with one another and are circumferentially-offset from one another along the elongated member.

The segmented contacts of a segmented-contact sets described herein include a stimulation portion and one or more retention members that collectively form a loop of material having at least two different arced portions. In at least some embodiments, the segmented contacts are electrically isolated from one another by insulation interleaved between the at least two different arced portions. In at least some embodiments, the insulation is interleaved between the stimulation region of a first segmented contact and the one or more retention members of the second segmented contact of the segmented-contact array.

Figure 5A:
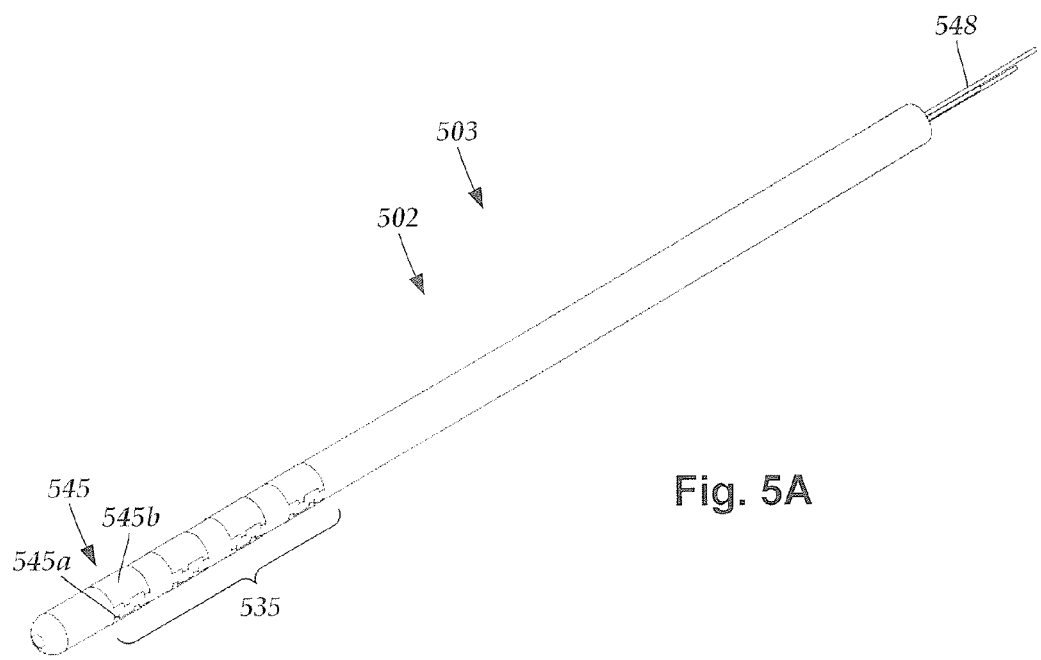
FIG. 5A is a schematic perspective view of one embodiment of proximal portion of a lead with segmented terminals, according to the invention.
Figure 5B:
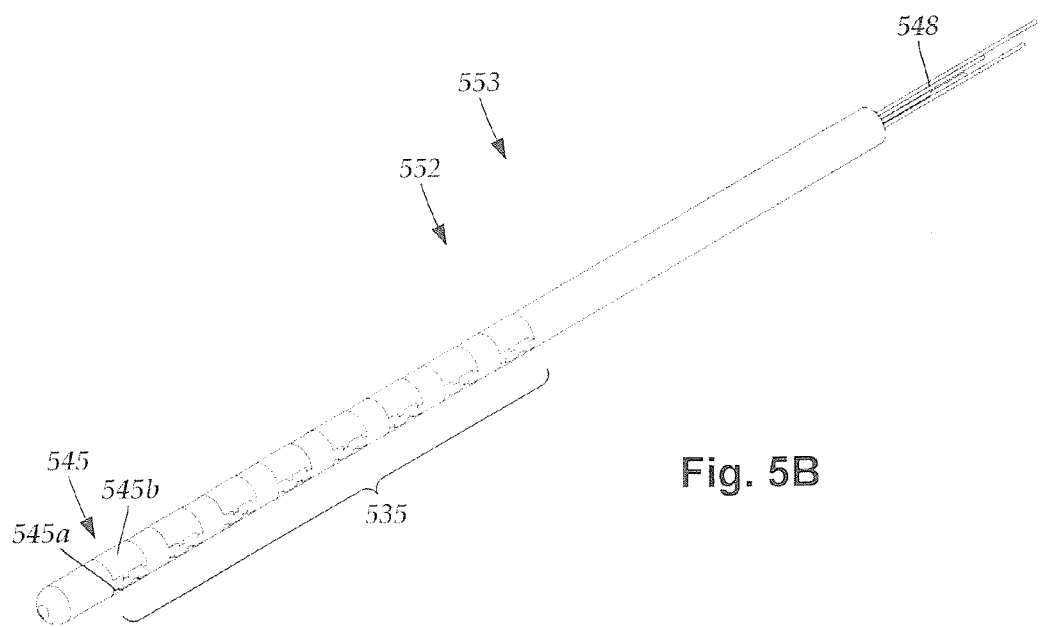
FIG. 5B is a schematic perspective view of another embodiment of proximal portion of a lead with segmented terminals, according to the invention.

In FIGS. 5A-5B, and in other figures, the segmented contacts are shown as being segmented terminals. It will be understood that the below discussion of segmented terminals applies also to segmented electrodes. In FIGS. 5A-5B, and in other figures, the segmented contacts are shown as being disposed along a lead. It will be understood that the segmented contacts can be disposed along any suitable elongated member including, for example, lead extensions, splitters, adaptors, or the like.

FIG. 5A illustrates, in schematic perspective view, one embodiment of a proximal portion 502 of a lead 503. An array of terminals 535 is disposed along the lead 503. The array of terminals 535 is configured and arranged to electrical couple to connector contacts of a connector, such as the connector contacts of the connector (744 in FIG. 7), when the lead 535 is received by the connector. At least one of the terminals of the terminal array 535 extends around less than an entire circumference of the lead 503. The terminal array 535 is coupled to one or more electrode arrays (625, 625a, and 625b in FIGS. 6A-6C) via conductors 548.

In at least some embodiments, the terminal array 535 includes at least one segmented-terminal set, such as segmented-terminal set 545 which, in turn, includes multiple segmented terminals, such as segmented terminals 545a and 545b. In at least some embodiments, the individual terminals of the segmented-terminal sets 545 have the same particular longitudinal position with one another along a length of the lead 503.

In some embodiments, the terminal array 535 is formed exclusively from segmented terminals. In other embodiments, the terminal array 535 includes a combination of one or more ring-shaped terminals and one or more segmented-terminal sets.

The terminal array 535 can include any suitable number of segmented-terminal sets including, for example, one, two, three, four, five, six, seven, eight, nine, ten eleven, twelve, thirteen, fourteen, fifteen, sixteen, or more segmented-terminal sets. In FIG. 5A, four segmented-terminal sets are shown disposed along the lead 503. FIG. 5B illustrates, in schematic perspective view, another embodiment of a proximal portion 552 of a lead 553. The terminal array 535 disposed along the lead 553 of FIG. 5B has eight segmented-terminal sets 545.

Figure 6A:
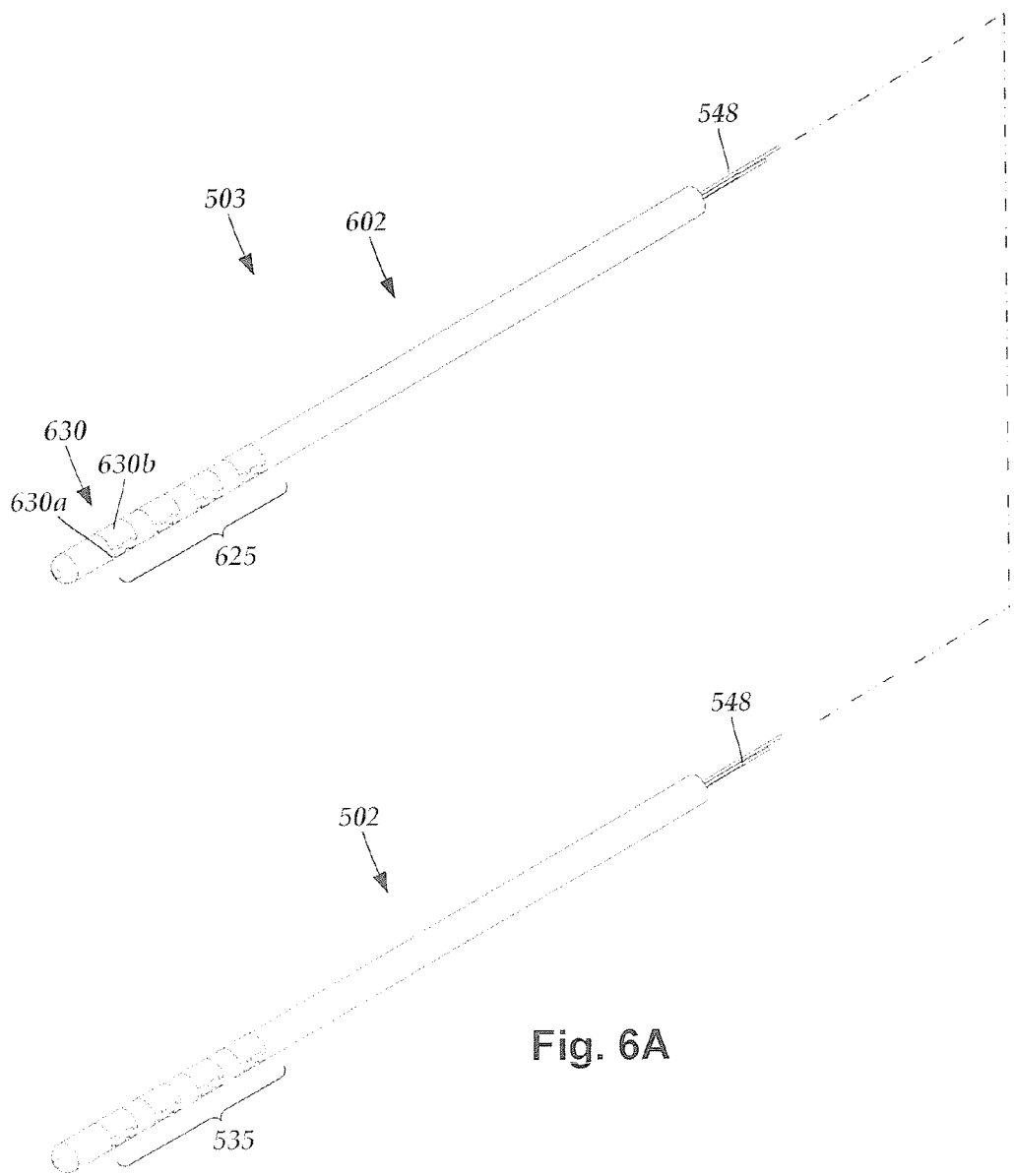
FIG. 6A is a schematic perspective view of one embodiment of a lead that includes the proximal portion of FIG. 5A, according to the invention.

Turning to FIG. 6A, the distal portions of elongated members with segmented-terminal sets can have any suitable electrode configuration (e.g., segmented electrodes, ring-shaped electrodes, or both). In at least some embodiments, the elongated members are percutaneous with a single distal portion and a single proximal portion.

FIG. 6A illustrates, in schematic perspective view, one embodiment of proximal 502 and distal 602 portions of the lead 503. An array of electrodes 625 is disposed along the distal portion 602 of the lead 503. The electrode array 625 can include any suitable number of electrodes. In at least some embodiments, the number of electrodes is equal to the number of terminals 535. In FIG. 6A, the electrode array 625 is shown as having eight electrodes. In at least some embodiments, the number of electrodes disposed along the electrode array 625 is not equal to the number of terminals disposed along the terminal array 535.

The electrodes of the electrode array 625 can be segmented, ring-shaped, or both. In FIG. 6A, the electrode array 625 is shown having multiple segmented-electrode sets, such as segmented-electrode set 630 which, in turn, includes multiple segmented electrodes, such as segmented electrodes 630a and 630b.

Figure 6B:
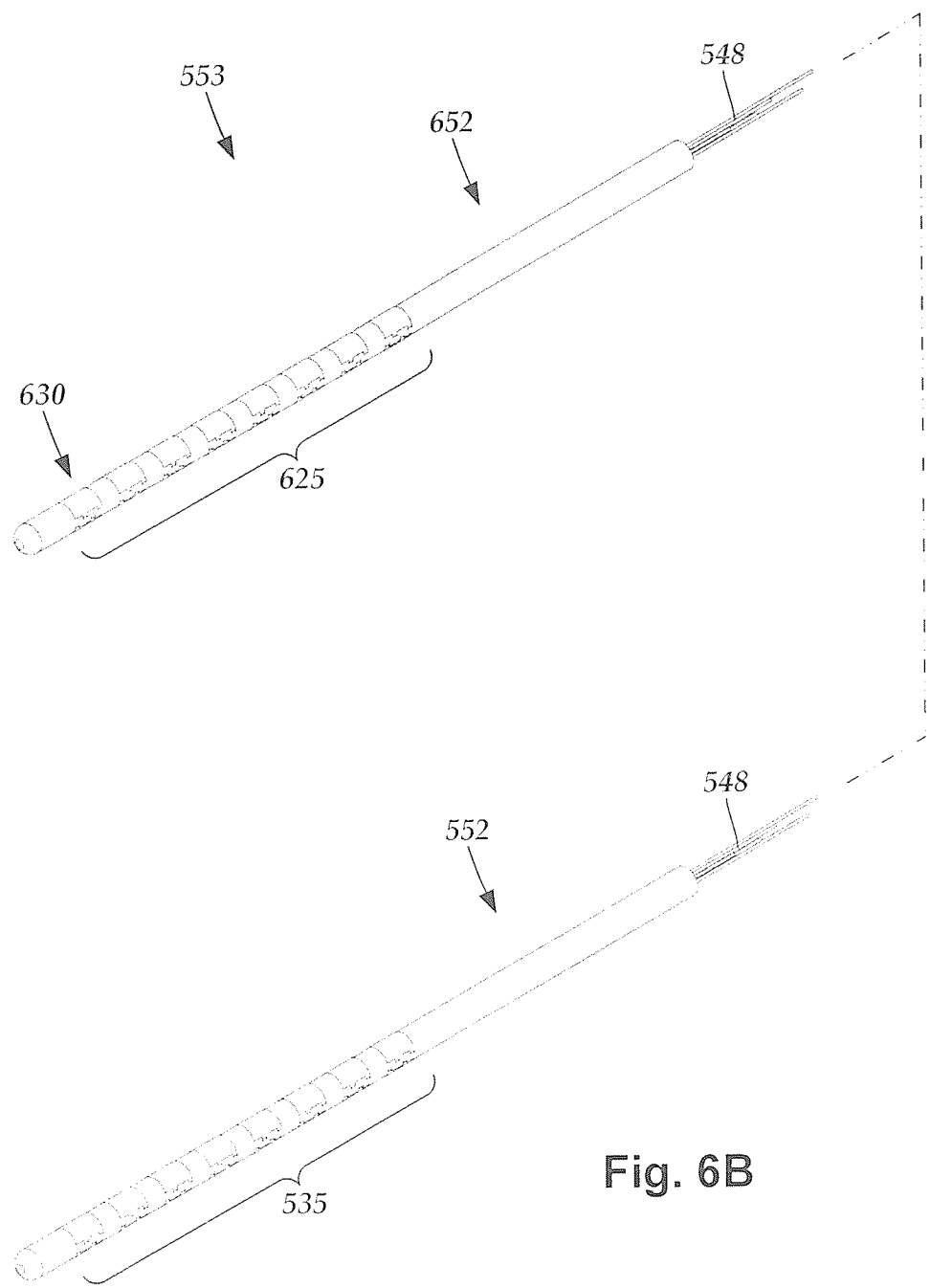
FIG. 6B is a schematic perspective view of one embodiment of a lead that includes the proximal portion of FIG. 5B, according to the invention.

Similarly, FIG. 6B illustrates, in schematic perspective view, another embodiment of proximal 552 and distal 662 portions of the lead 553. The electrode array 625 is shown in FIG. 6B as having sixteen electrodes arranged into eight segmented-electrode sets 630. In FIG. 6B, the number of electrodes disposed along the electrode array 625 is shown as being equal to the number of terminals disposed along the terminal array 535.

Figure 6C:
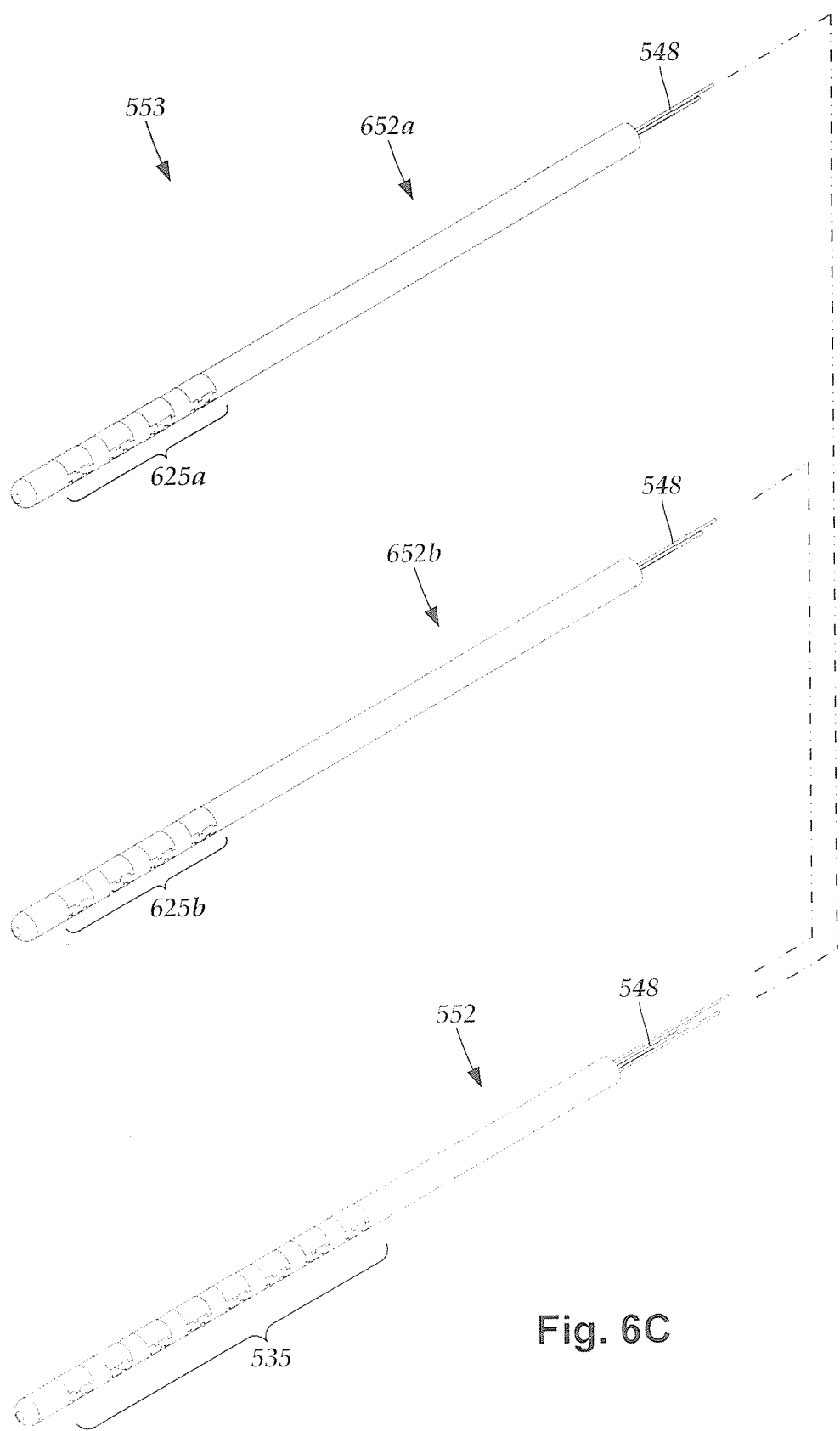
FIG. 6C is a schematic perspective view of another embodiment of a lead that includes the proximal portion of FIG. 5B, according to the invention.

Turning to FIG. 6C, in at least some embodiments the elongated member includes a single proximal portion and multiple distal portions. One advantage of implementing segmented terminals is that it may increase the number of terminals disposed along a lead from conventional leads. The increased number of terminals may enable the lead to be designed with multiple distal portions, where a different electrode array is disposed along each of the distal portions, and where electrodes of each of the multiple electrode arrays are coupled to terminals disposed along a single proximal portion. Such a design may be useful, for example, in deep brain stimulation where bilateral stimulation is common.

When the lead has multiple distal portions and a single proximal portion with segmented terminals, the single proximal portion can be received by a single connector port. Such an arrangement enables each of multiple electrode arrays disposed along different distal portions to be operated by a single control module. Additionally, such a design enables multiple electrode arrays to be controlled by a single control module via a single connector with a single lead-receiving port.

FIG. 6C illustrates, in schematic perspective view, yet another embodiment of the lead 553. In FIG. 6C, the lead 553 is shown having the proximal portion 552 and two distal portions 652a and 652h. An electrode array 625a is disposed along the distal portion 652a and an electrode array 625b is disposed along the distal portion 652b. Electrodes of each of the electrode arrays 625a, 625b are coupled to terminals of the terminal array 535. In FIG. 6C, two distal lead portions are shown. It will be understood that the lead can include any suitable number of distal portions coupled to a single proximal portion.

Figure 7:
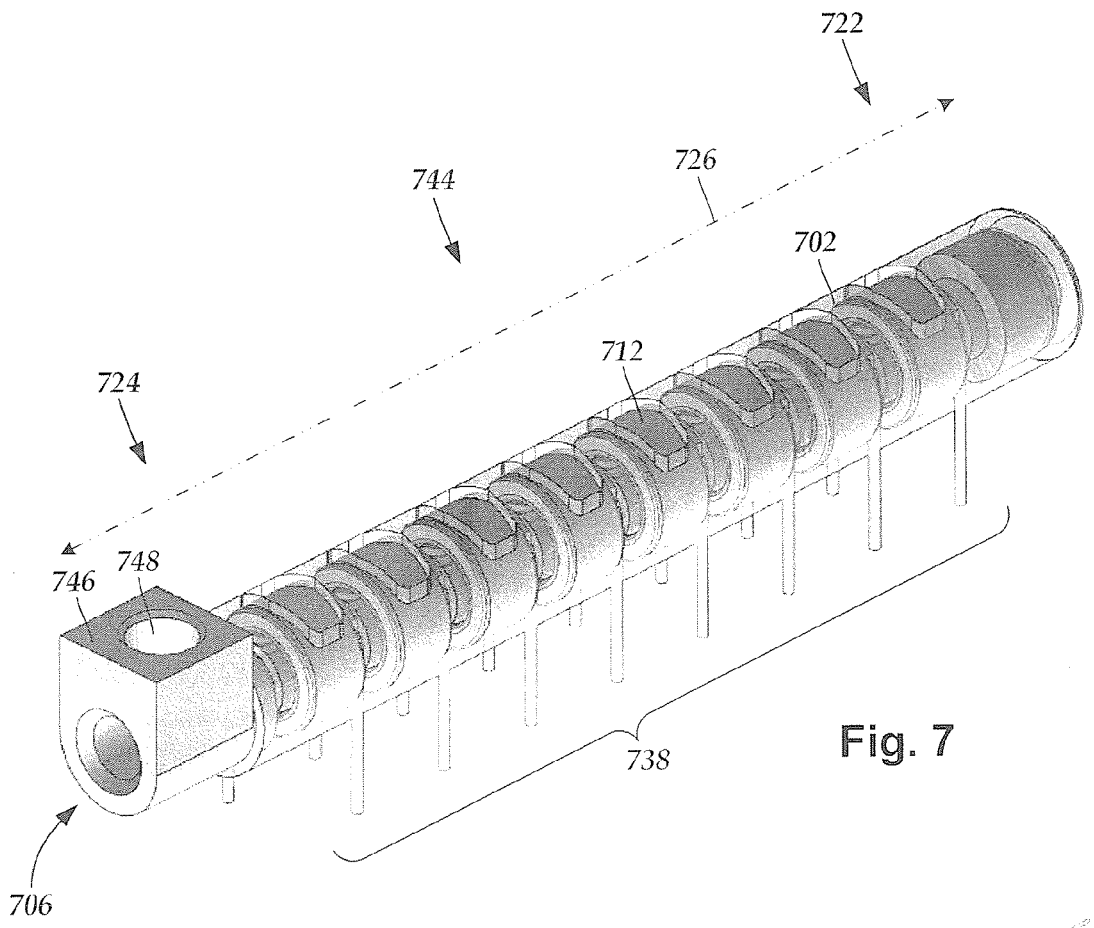
FIG. 7 is a schematic perspective view of one embodiment of a connector suitable for use with any of the implantable leads of FIGS. 6A-6C, according to the invention.

Turning to FIG. 7, the proximal portions of the elongated members, such as the leads 503, 553, are typically inserted into connectors disposed along a lead extension, control module, adaptor, splitter, or the like. In at least some embodiments, a connector suitable for receiving the proximal portion of an elongated member (e.g., the leads 503, 553) with segmented terminals includes connector-contact sets having segmented connector contacts suitable for coupling with the segmented terminals. Examples of connectors with segmented connector contacts can be found in, for example, U.S. patent application Ser. No. 62/077,762, filed on even date herewith, entitled "Systems and Methods for Making and Using Improved Connector Contacts for Electrical Stimulation Systems" which is incorporated by reference.

FIG. 7 illustrates, in schematic perspective view, one embodiment of a connector 744 suitable for receiving the proximal portion 552 of the lead 553. The connector 744 can be disposed, for example, on a control module, lead extension, adaptor, splitter, or the like. The connector 744 has a first end 722, an opposing second end 724, and a longitudinal length, shown in FIG. 7 by a dashed and dotted line 726. The connector 744 includes an elongated connector housing 702 that defines a connector lumen 706 suitable for receiving a portion of an elongated member, such as the lead 503, 553; a lead extension (e.g., 324 in FIG. 3C'); or the like. In FIG. 7, the connector lumen 706 is defined along the second end 724 of the connector 744 and extends along the longitudinal length 726 of the connector 744. The first end 722 of the connector 744 can be either open or closed.

Multiple connector-contact assemblies, such as connector-contact assembly 712, are disposed in a spaced-apart relationship along the longitudinal length 726 of the connector housing 702 such that the connector-contact assemblies 712 are exposed to the connector lumen 706 and also to an array of conductive members 738 that couple the connector contacts to other components. When, for example, the connector 744 is disposed on a lead extension (e.g., 324 in FIG. 3C), the conductive members 738 may couple the connector-contact assembly 712 to lead extension terminals. When, for example, the connector 744 is disposed on a control module, the conductive members 738 may couple the connector-contact assembly 712 to the electronic subassembly (110 in FIG. 1). In at least some embodiments, the conductive members 738 couple the connector-contact assembly 712 to the electronic subassembly (110 in FIG. 1) via feedthrough pins extending through the sealed housing (114 in FIG. 1)

Optionally, a retention block 746 is disposed along the connector 744. The retention block 746 can be used to facilitate retention of an elongated member when the elongated member is inserted into the connector lumen 706. In at least some embodiments, the retention block 746 defines a fastening aperture 748 configured to receive a fastener (e.g., a set screw, pin, or the like). In at least some embodiments, the fastener, when received by the fastener aperture 748, is configured to tighten against a portion of the elongated member (e.g., a retention sleeve) when the elongated member is inserted into the connector lumen 706.

Figure 8:
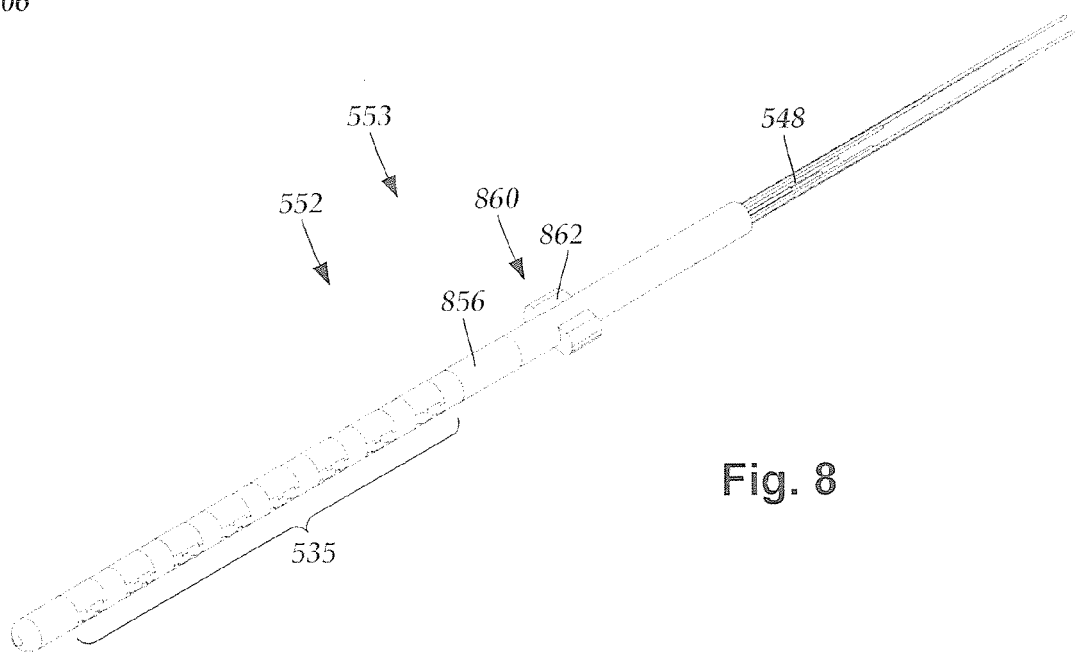
FIG. 8 is a schematic view of one embodiment of an alignment assembly disposed along the proximal portion of the lead of FIG. 5B, according to the invention.

Turning to FIG. 8, in at least some embodiments the elongated member includes an alignment assembly to facilitate connection of the elongated member to the connector. FIG. 8 illustrates, in schematic perspective view, one embodiment of the proximal portion 552 of the lead 553. Optionally, the electrical stimulation system includes an alignment assembly 860 to ensure that, when the elongated member includes one or more segmented-terminal sets, the segmented terminals of the one or more segmented-terminal sets are aligned circumferentially with the segmented connector contacts (see e.g., 1020a, 1020b of FIG. 10C) of the connector. Circumferentially-aligning the segmented terminals with the segmented connector contacts may serve to prevent undesired electrical connections (e.g., short-circuiting) between the connector contacts and undesired terminals, or other connector contacts, or both.

In at least some embodiments, the alignment assembly includes one or more alignment elements (e.g., circumferentially-alignable markers, matable elements, or the like) that are disposed along the proximal portion of the elongated member, or along a portion of the connector, or both, and that can be used to visually identify the circumferential orientation of the segmented terminals relative to the segmented connector contacts when the elongated member is being inserted into the connector.

Note that the circumferential orientation of the segmented connector contacts relative to the connector can be known and can also be constant. In which case, the circumferential orientation of the segmented connector contacts can be determined by viewing the circumferential orientation of the connector. In at least some embodiments, the connector block (746 in FIG. 7) is a visually distinct element along the exterior of the connector that can be used as a circumferential marker.

In FIG. 8, and in other figures, the alignment assembly 860 includes alignment members 862 extending outwardly from circumferentially-opposed portions of the elongated member. In at least some embodiments, the alignment members 862 are visually aligned relative to the retention block (746 in FIG. 7).

In at least some embodiments, the alignment assembly includes two or more matable elements (e.g., one or more notches/grooves, tabs/slots, or the like), where one element of the matable elements is disposed along the elongated member, and the other element of the matable elements is disposed along the connector. In at least some embodiments, the retention block (746 in FIG. 7) includes one or more grooves, or slots, or the like, that are configured to only mate with the alignment members 762 of the elongated member when the segmented terminals of the elongated member are oriented circumferentially with the segmented connector contacts of the connector. The alignment assembly can include any suitable number of alignment members including, for example, one, two, three, four, five, six, seven, eight, or more alignment members.

The alignment assembly can be disposed along any suitable portions of the elongated member, connector, or both. For example, in at least some embodiments at least one of the alignment members is disposed distal to distal-most terminal of the terminal array 535. Additionally, or alternately, one or more alignment members may be disposed proximal to the distal-most terminal of the terminal array 535. In at least some embodiments, at least one of the alignment members is disposed at the proximal tip of the elongated member, or proximal to the proximal-most terminal of the terminal array 535. In at least some embodiments, at least a portion of the alignment assembly is disposed along the second end (724 in FIG. 7) of the connector 744. Additionally, or alternately, one or more portions of the alignment assembly may be disposed in the connector along any suitable portion of the connector lumen (706 in FIG. 7). For example, one or more grooves or channels may extend along the longitudinal length of the connector within the connector lumen and may be configured to mate with the alignment members of the elongated member.

Optionally, a retention sleeve 856 is disposed along the proximal portion 552 of the lead 553. The retention sleeve 856 is configured and arranged to facilitate retention of the lead by the connector when the lead is received by the connector. The retention sleeve 756 is typically formed from a material that is harder than the material of the lead body and is configured to be tightened between a fastener received by the fastener aperture (748 in FIG. 7) and a side wall of the connector lumen (706 in FIG. 7). The retention sleeve 856 may be positioned at any suitable location along the lead including, for example, distal to the distal-most terminal of the terminal array 535. The alignment members may be disposed proximally, distally, or both, to the retention sleeve 856.

Figure 9:
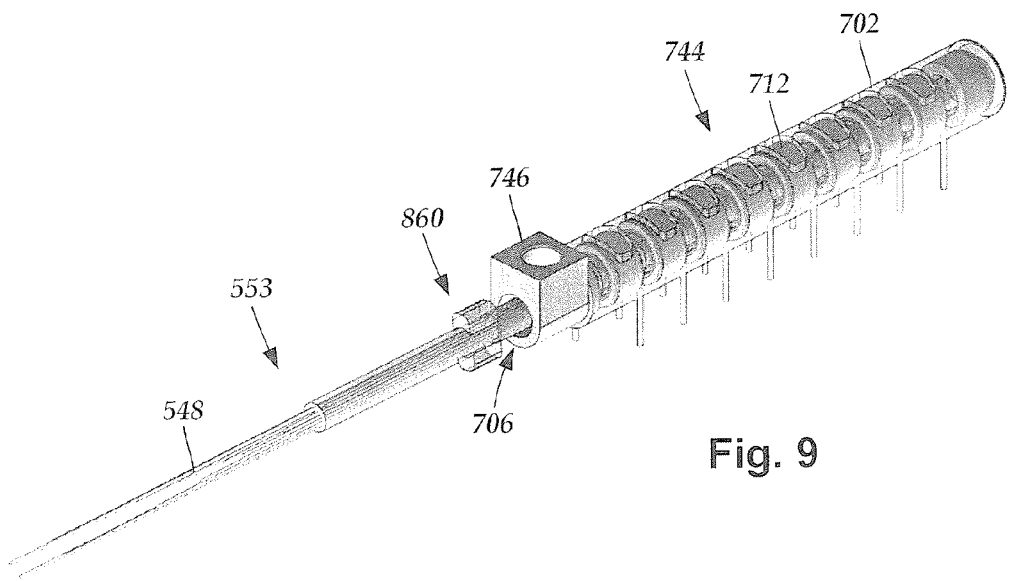
FIG. 9 is a schematic perspective view of one embodiment of the proximal portion of the lead of FIG. 8 disposed in the connector of FIG. 7, according to the invention.

FIG. 9 illustrates, in schematic perspective view, one embodiment of the proximal portion of the lead 553 received by the connector 744. In at least some embodiments, the alignment assembly 860 is aligned with the retention block 746 for ensuring that the segmented terminals of the terminal array (535 in FIGS. 5 and 8) of the lead 553 are circumferentially-aligned with segmented connector contacts (see e.g., 1020a, 1020b of FIG. 10C) of the connector-contact assemblies 712.

Figure 10A:
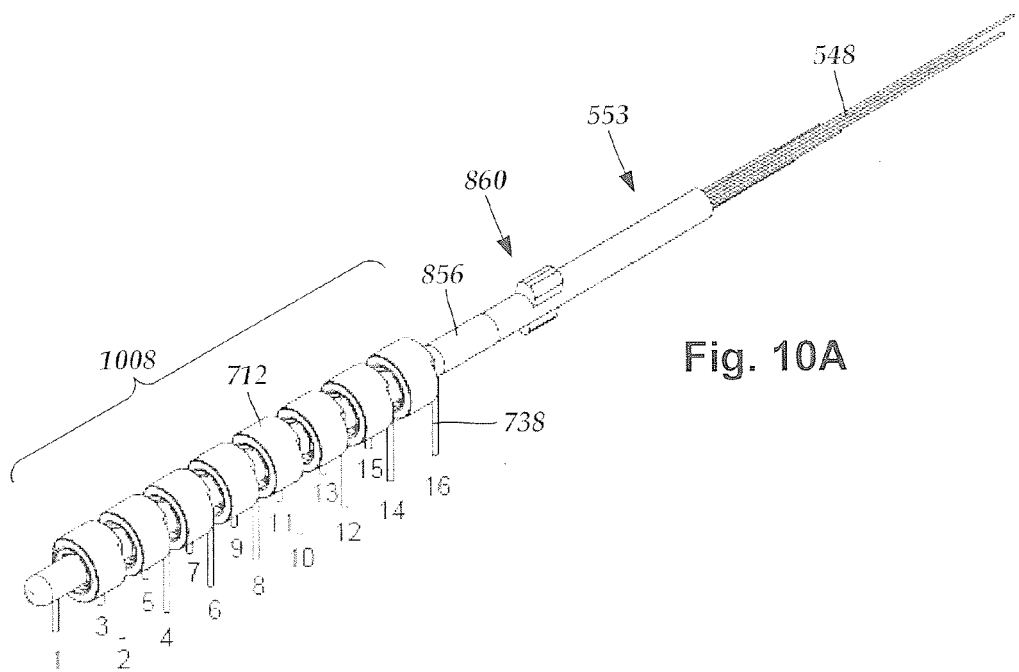
FIG. 10A is a schematic perspective view of one embodiment of terminals of the lead of FIG. 8 coupled to connector-contact assemblies of the connector of FIG. 7, according to the invention.
Figure 10B:
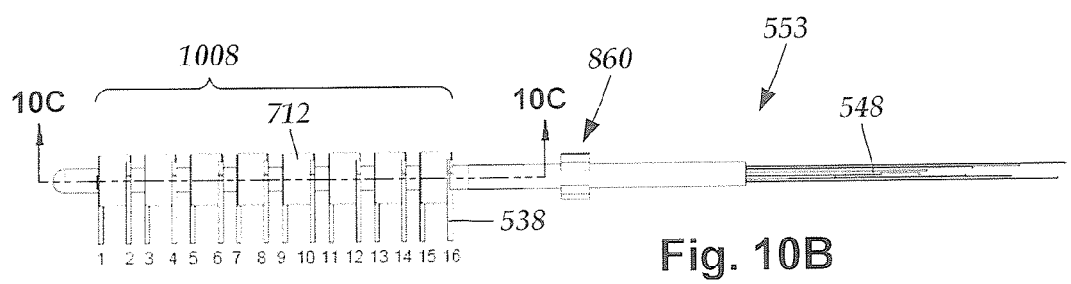
FIG. 10B is a schematic side view of one embodiment of terminals of the lead of FIG. 8 coupled to connector-contact assemblies of the connector of FIG. 7, according to the invention.
Figure 10C:
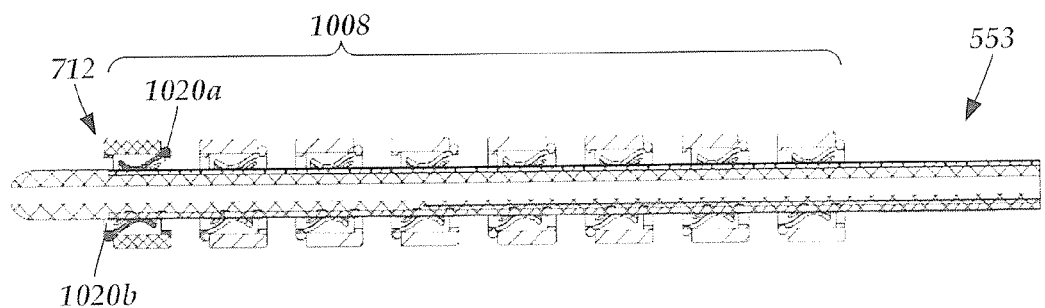
FIG. 10C is a schematic longitudinal cross-sectional view of one embodiment of terminals of the lead of FIG. 8 coupled to connector-contact assemblies of the connector of FIG. 7, according to the invention.

Turning to FIGS. 10A-10C, in at least some embodiments the connector-contact assemblies 712 of the connector (744 in FIGS. 7 and 9) are configured into a longitudinally-spaced-apart arrangement that facilitates making electrical contact with segmented terminals. FIGS. 10A-10C show several different views of the lead 553 disposed in the connector 744. In each of FIGS. 10A-10C, the connector housing 702 of the connector 744 is removed to more clearly show one embodiment of the connector-contact assemblies 712 of the connector 744.

FIG. 10A illustrates, in perspective view, one embodiment of terminals of the lead 553 coupled to connector-contact assemblies 712 of the connector (744 in FIG. 13). FIG. 10B illustrates, in side view, one embodiment of terminals of the lead 553 coupled to the connector-contact assemblies 712. FIG. 10C illustrates, in longitudinal cross-sectional view, one embodiment of terminals of the lead 553 coupled to connector-contact assemblies 712.

FIGS. 10A-10C show multiple connector-contact assemblies, such as connector-contact assembly 712, arranged into an array 1008 of connector-contact assemblies 712 that corresponds to the longitudinal arrangement of the segmented-terminal sets of the terminal array 535. Additionally, the connector-contact assemblies each include segmented connector contacts, such as segmented connector contacts 1020a, 1020b, that correspond to the circumferential relationship of the individual segmented terminals of the segmented-terminal sets.

Figure 11:
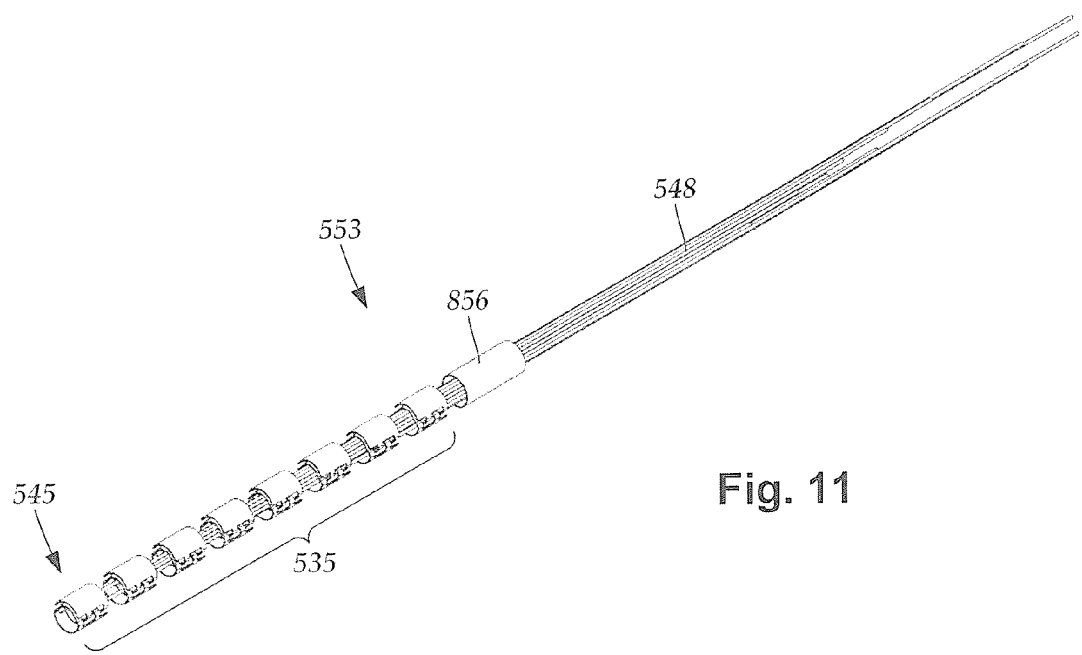
FIG. 11 is a schematic perspective view of one embodiment of the proximal portion of the lead of FIG. 5B with lead material removed to show a terminal array, conductors, and a retention sleeve of the lead, according to the invention.

Turning to FIG. 11, in at least some embodiments forming an elongated member with segmented contacts includes disposing an array of segmented contacts along a portion of the elongated member. FIG. 11 illustrates, in schematic perspective view, one embodiment of the proximal portion of the lead 553 with material of the lead removed, for clarity of illustration. The terminal array 535 and the optional retention sleeve 856 are disposed along the proximal portion of the lead 553. The terminal array 535 includes multiple segmented-terminal sets 545.

Figure 12:
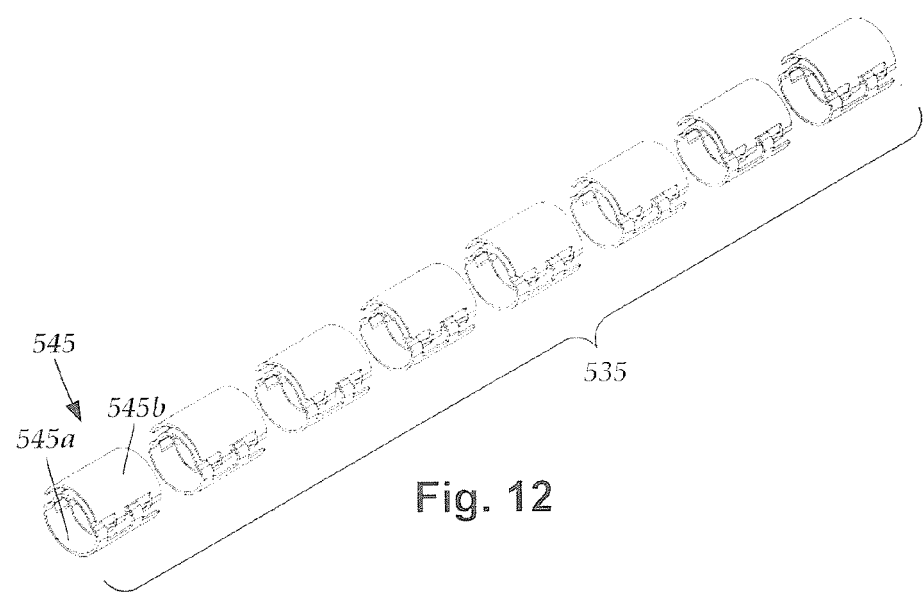
FIG. 12 is a schematic perspective view of one embodiment of the terminal array of FIG. 11, the terminal array including multiple segmented terminals arranged into segmented-terminal sets, according to the invention.

FIG. 12 illustrates, in schematic end view, one embodiment of the terminal array 535. The terminal array 535 includes multiple segmented-terminal sets 545. Each of the segmented-terminal sets 545 includes multiple terminals, such as terminals 545a and 545b, which are electrically isolated from one another and circumferentially-offset from one another.

Figure 13A:
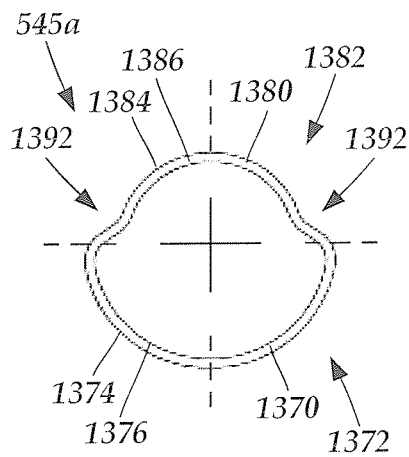
FIG. 13A is a schematic end view of one embodiment of one of the segmented terminals of the terminal array of FIG. 12, according to the invention.
Figure 13B:
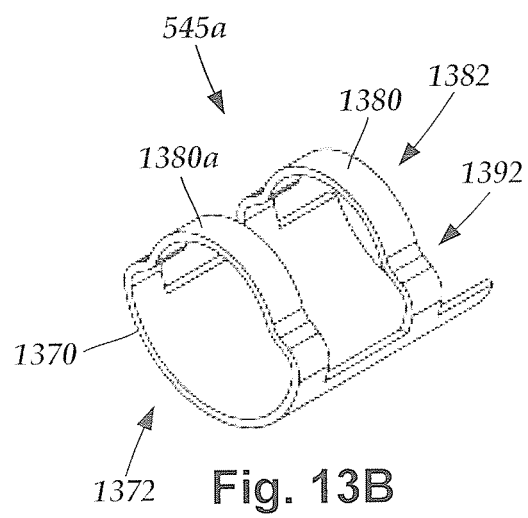
FIG. 13B is a schematic perspective view of one embodiment of one of the segmented terminals of FIG. 12, according to the invention.
Figure 13C:
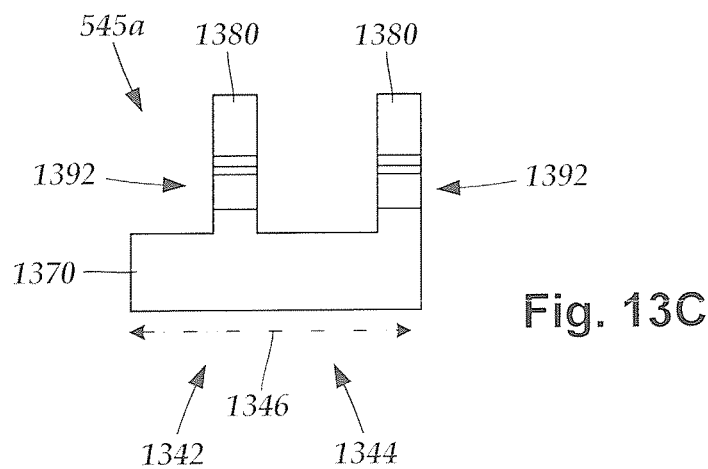
FIG. 13C is a schematic side view of one embodiment of one of the segmented terminals of FIG. 12, according to the invention.

FIGS. 13A-13C show one embodiment of a segmented contact suitable for use in forming the segmented-contact set. In at least some embodiments, each segmented contact of the segmented-contact set has the same size and shape as each of the remaining segmented contacts of the segmented-contact set.

FIG. 13A illustrates, in schematic end view, one embodiment of the segmented terminal 545a. FIG. 13B illustrates, in schematic perspective view, one embodiment of the segmented terminal 545a. FIG. 13C illustrates, in schematic side view, one embodiment of a side view of the segmented terminal 545a. The segmented terminal 545a includes a first end 1342, an opposing second end 1344, and a longitudinal length 1346.

The segmented terminal 545a includes a stimulation portion 1370 and one or more retention members 1380 coupled to the stimulation portion 1370. The stimulation portion 1370 and the one or more retention members 1380 collectively form a loop of material. In at least some embodiments, the loop of material is not circular. As discussed in more detail below, in at least some embodiments the loop of material includes at least two arced portions, where each arc portion has a different curvature. In some embodiments, the loop is an open-loop (e.g., C-shaped). In other embodiments, the loop is a closed-loop. In at least some embodiments, the one or more retention members 1380 couple to the stimulation portion 1370 along opposing longitudinal edges of the stimulation portion 1370, as shown in FIGS. 13A-13C.

The stimulation portion 1370a includes an outer stimulation surface 1374 and an opposing inner surface 1376. In at least some embodiments, the stimulation portion 1370a is configured to correspond to the size and shape of the lead such that the outer stimulation surface 1374 of the segmented electrode is flush with the outer surface of the lead. The one or more retention members 1380a include an outer surface 1384 and an opposing inner surface 1386.

The segmented terminals can include any suitable number of retention members 1380 including, for example, one, two, three, four, five, or more retention members. In FIGS. 13A-13C, and in other figures, the segmented electrodes are shown as having two retention members 1380. As will be discussed in more detail below, in at least some embodiments the one or more retention members 1380*a* are configured to remain within the body of the lead during operation.

In at least some embodiments, the stimulation portion 1370 forms a first arced portion 1372 of the segmented electrode. In at least some embodiments, the one or more retention members 1380 form second arced portions 1382 of the segmented electrode. In at least some embodiments, the first arced portion 1372 corresponds to the curvature of the lead such that the stimulation portion 1370 is flush with an outer surface of the lead. In at least some embodiments, the first arced portion 1372 has a different curvature than the second arced portion 1382. In at least some embodiments, the second arced portion(s) 1382 has a curvature that enables the one or more retention members 1380 to remain within the body of the lead while the stimulation portion 1370 is exposed along the outer surface of the lead.

In at least some embodiments, the one or more retention members 1380 include one or more transition regions 1392 that transition the segmented electrode between curvature the first arced portion 1372 and the curvature of the second arced portion 1382. In at least some embodiments, the one or more transition regions 1392 includes an arced portion that is different from at least one of the first arced portion 1372 or the second arced portion 1382. In at least some embodiments, the one or more transition regions 1392 includes an arced portion that is different from each of the first arced portion 1372 and the second arced portion 1382. In at least some embodiments, the arced portion of the one or more transition regions 1392 is concave when viewed from a position external to the segmented terminal 545*a*, while the first arced portion 1372 and the second arced portion 1382 are both convex when viewed from a position external to the segmented terminal 545*a*.

In at least some embodiments, the first arced portion 1372 is disposed opposite to the second arced portion 1382. In at least some embodiments, the smallest linear distance between opposing ends of the first arced portion 1372 is greater than the smallest linear distance between opposing ends of the second arced portion 1382.

Figure 14A:
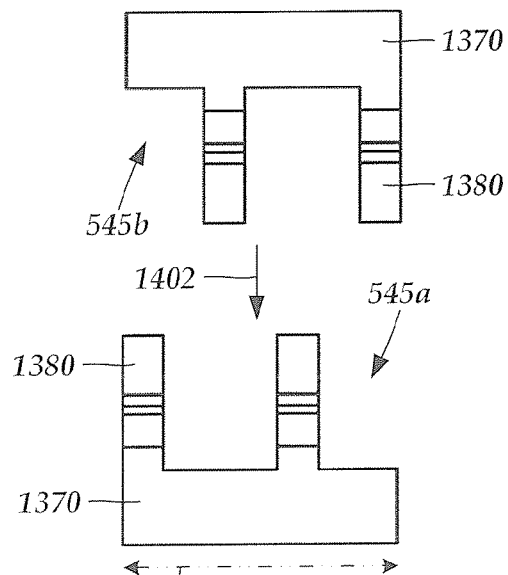
FIG. 14A is a schematic side view of one embodiment of two segmented terminals, including the segmented terminal of FIGS. 13A-13C, arranged such that the segmented terminal are flipped longitudinally and circumferentially-rotated 180° relative to one another, according to the invention.
Figure 14B:
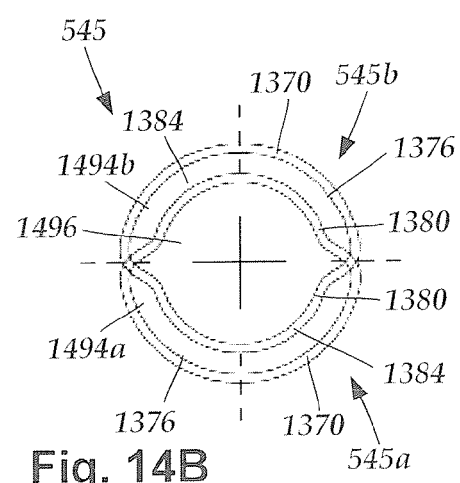
FIG. 14B is a schematic end view of one embodiment of the segmented terminals of FIG. 14A brought closer together to form one of the segmented-terminal sets of FIG. 12, according to the invention.
Figure 14C:
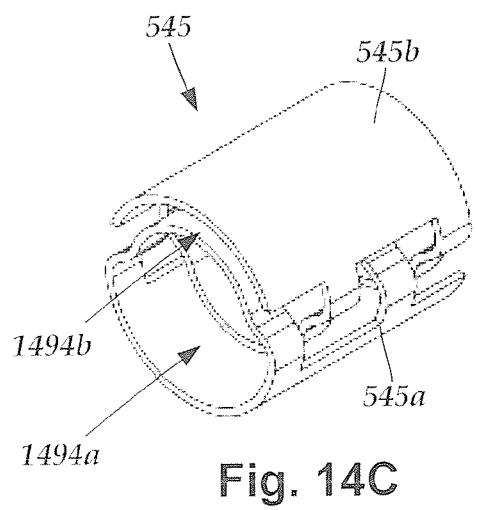
FIG. 14C is a schematic perspective view of one embodiment of the segmented-terminal set of FIG. 14A, according to the invention.

Turning to FIG. 14A, the segmented terminals are suitable for arranging into segmented-terminal sets. In FIGS. 14A-14C, and in other figures, the segmented-terminal sets are shown having two terminals that are similar to one another in shape and size, and that are arranged into an operational configuration with the individual segmented terminals being longitudinally- and circumferentially-opposed to one another. The configuration and arrangement of segmented terminal 545*a* described above with respect to FIGS. 13A-13C is also applicable to both segmented terminals 545*a* and 545*b* illustrated in FIGS. 14A-14C.

FIG. 14A illustrates, in schematic side view, one embodiment of the segmented terminals 545*a* and 545*b* arranged into the segmented-terminal set 545. In FIG. 14A, the segmented terminal 545*a* is shown flipped along its longitudinal length 1346 and circumferentially rotated 180° relative to the segmented terminal 545*b*. As shown by arrow 1402, the segmented terminals 545*a* and 454*b* can be brought closer together to form the segmented-terminal set 545.

In at least some embodiments, the one or more retention members 1380 of each of the segmented terminals are arranged longitudinally along the opposing longitudinal edges of the stimulation portion 1370 of their respective segmented electrodes such that the retention member(s) 1380 of the segmented terminal 545*a* do not physically obstruct the retention member(s) 1380 of the segmented terminal 545*b*, and vice versa, when the segmented terminals brought into the operational configuration shown in FIGS. 14B-14C.

FIG. 14B illustrates, in schematic end view, one embodiment of the segmented terminals 545*a* and 545*b* arranged into the segmented-terminal set 545. FIG. 14C illustrates, in schematic perspective view, one embodiment of the segmented-terminal set 545. In FIGS. 14B-14C, and in other figures, the segmented electrodes 545*a* and 545*b* are arranged into an operational configuration such that the segmented terminal 545*a* is flipped along its longitudinal length 1346 and circumferentially rotated 180° relative to segmented terminal 545*b*.

As shown in FIG. 14B, when the segmented terminals 545*a*, 545*b* are arranged into their operational configuration, the loop-shapes of the segmented terminals 545*a*, 545*b* form a shape similar to a Venn diagram, with three open spaces formed between portions of the segmented terminals 545*a*, 545*b*. As shown in FIGS. 14B-14C, when the segmented terminals 545*a*, 545*b* are arranged into their operational configuration, opposing retention spaces 1494*a*, 1494*b* are formed between the outer surfaces 1384 of the retention members 1380 and the inner surfaces 1376 of the stimulation portion 1370. In FIGS. 14A-14B, the retention space 1494*a* is shown between the retention member 1380 of the segmented terminal 545*b* and the stimulation portion 1370 of the segmented terminal 545*a*; and the retention space 1494*b* is shown between the retention member 1380 of the segmented terminal 545*a* and the stimulation portion 1370 of the segmented terminal 545*b*. Additionally, when the segmented terminals 545*a*, 545*b* are arranged into their operational configuration, a central aperture 1496 is formed. In at least some embodiments, the central aperture 1496 is configured and arranged to receive at least one conductor (548 in FIGS. 5A-5B).

FIGS. 15A-19B show one of many possible techniques for forming an elongated member having a contact array with at least one segmented-contact set. FIG. 15A illustrates, in schematic perspective view, one embodiment of a conductor 548*a* of the plurality of conductors (548 in FIGS. 5A-5B) coupled to the segmented terminal 545*a*. FIG. 15B illustrates, in close-up schematic perspective view, one embodiment of the conductor 548*a* coupled to the segmented terminal 545*a*. FIG. 15C illustrates, in schematic end view, one embodiment of the conductor 548*a* coupled to the segmented terminal 545*a*. In FIGS. 15A-15C, and in other figures, the conductor 548*a* is shown coupled to the inner surface 1386 of at least one of the retention members 1380. This is discussed in more detail below, with reference to FIGS. 16A-17C.

Figure 16A:
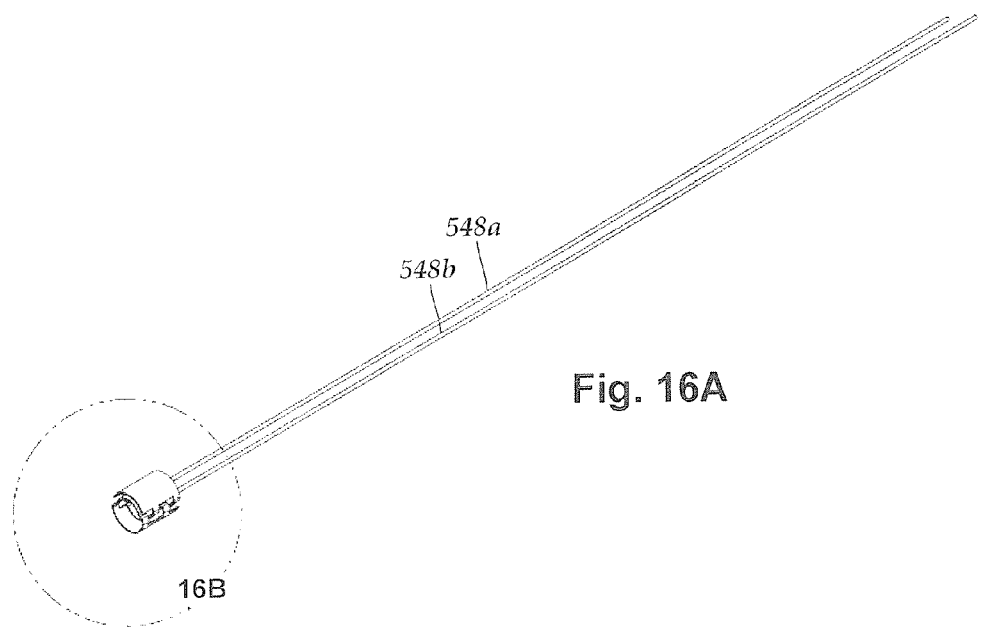
FIG. 16A is a schematic perspective view of one embodiment of multiple conductors coupled to the segmented-terminal set of FIGS. 14A-14B, according to the invention.
Figure 16B:
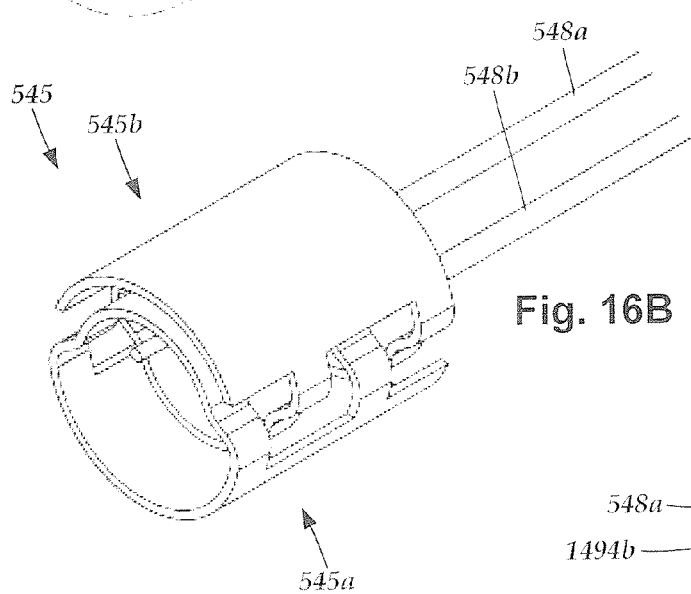
FIG. 16B is a schematic close-up perspective view of one embodiment of multiple conductors coupled to the segmented-terminal set of FIGS. 14A-14B, according to the invention.
Figure 16C:
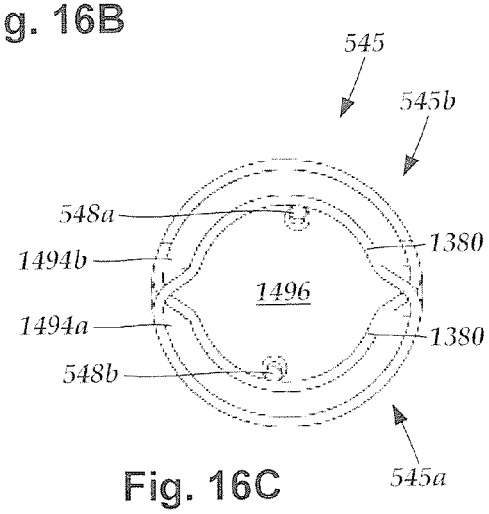
FIG. 16C is a schematic end view of one embodiment of multiple conductors coupled to the segmented-terminal set of FIGS. 14A-14B, according to the invention.

FIG. 16A illustrates, in schematic perspective view, one embodiment of the conductors 548*a*, 548*b* coupled to the segmented electrodes 545*a*, 545*b*, respectively, of the segmented-terminal set 545. FIG. 16B illustrates, in schematic close-up perspective view, one embodiment of the conductors 548*a*, 548*b* coupled to the segmented-terminal set 545. FIG. 16C illustrates, in schematic end view, one embodiment of the conductors 548*a*, 548*b* coupled to the segmented-terminal set 545.

At least one conductor of the plurality of conductors (548 in FIGS. 5A-5B) is coupled to each terminal of the terminal array (535 in FIGS. 5A-5B). In at least some embodiments, a single different conductor of the plurality of conductors is coupled to each terminal. The conductor(s) can be coupled to the terminals using any suitable technique including, for example, welding, soldering, crimping, conductive adhesive, or the like or combinations thereof.

As mentioned above, the conductor(s) can be coupled to the terminals along any suitable portions of the terminals. In at least some embodiments, the terminals are entirely formed from conductive materials. As will be discussed in more detail below with reference to FIGS. 17A-17C, in at least some embodiments insulation is disposed along portions of the segmented-terminal sets to electrically isolate the segmented terminals from one another. Consequently, it may be advantageous to couple the conductors to their respective terminals along portions of the terminals that do not physically obstruct the insulation. In at least some embodiments, the conductors are attached to the terminals along one or more of the retention members 1380. In at least some embodiments, and as shown in each of FIGS. 15A-16C, at least one of the conductors is attached to at least one of the terminals along the inner surface 1386 of one or more of the retention members 1380.

Figure 17A:
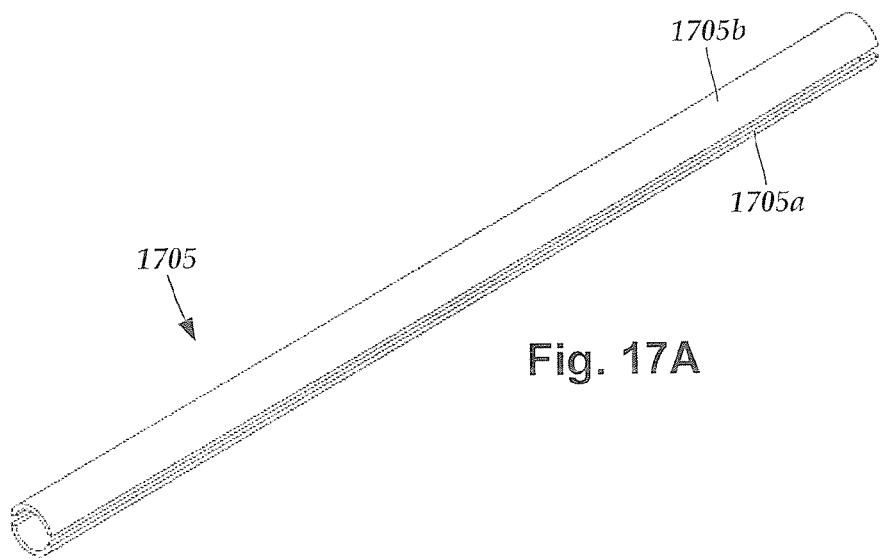
FIG. 17A is a schematic perspective view of one embodiment of insulation suitable for disposing between individual segmented terminals of segmented-terminal sets of the terminal array of FIG. 12, according to the invention.

Turning to FIG. 17A, in at least some embodiments insulation is used to electrically isolate individual terminals of the segmented-terminal sets from one another. The insulation may also be used to maintain the configuration of the individual terminals of the segmented-terminal set relative to one another.

Figure 17B:
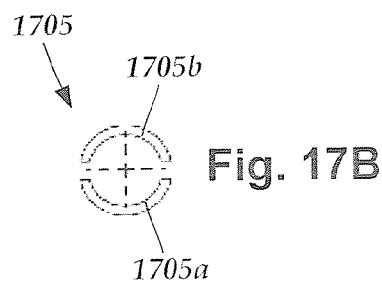
FIG. 17B is a schematic end view of one embodiment of the insulation of FIG. 17A, according to the invention.
Figure 17C:
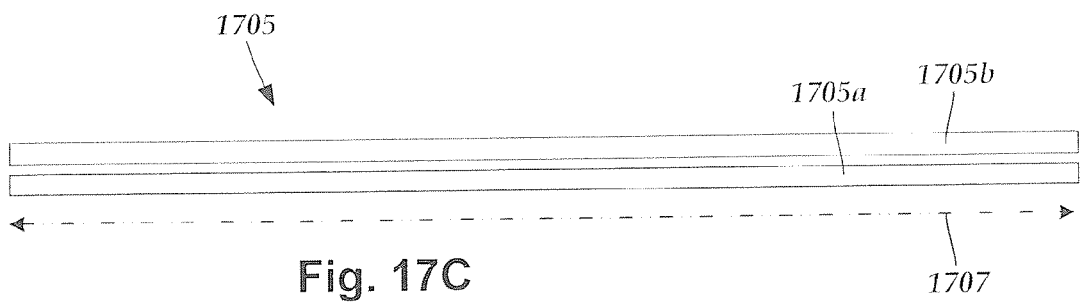
FIG. 17C is a schematic side view of one embodiment of the insulation of FIG. 17A, according to the invention.

FIG. 17A illustrates, in schematic perspective view, one embodiment of insulation 1705 suitable for electrically-isolating two or more segmented terminals from one another. FIG. 17B illustrates, in schematic end view, one embodiment of the insulation 1705. FIG. 17C illustrates, in schematic side view, one embodiment of the insulation 1705. The insulation can be formed in any suitable shape. In at least some embodiments, the insulation includes insulating members formed as one or more elongated substrates, or sheets, of material.

Any suitable number of insulating members may be used. In at least some embodiments, the number of insulating members is equal to the number of contacts of the one or more segmented-contact sets. In FIGS. 17A-7C, the insulation 1705 is shown as including two insulating members 1705a and 1705b. The insulation can be formed from any suitable nonconductive material suitable for use with implantable medical devices (e.g., one or more thermoplastic polymers, or the like).

In at least some embodiments, the insulation 1705 has a longitudinal length 1707 that is no less than a longitudinal length of the terminal array (535 in FIGS. 5A-5B). In at least some embodiments, the insulation 1705 has a longitudinal length 1707 that is no less than the linear distance between a distal most segmented-terminal set and a proximal end of the retention sleeve (856 in FIG. 8).

Turning to FIG. 18A, in at least some embodiments the insulation is suitable for disposing along the retention spaces (1494a, 1494b in FIGS. 14A-14B) formed between the segmented terminals of the segmented-terminal set when the segmented terminals are disposed in an operational configuration. FIG. 18A illustrates, in schematic perspective view, one embodiment of the insulation 1705 disposed between portions of the segmented terminals 545a, 545b of the segmented-terminal set 545. FIG. 18B illustrates, in schematic close-up perspective view, one embodiment of the insulation 1705 disposed between portions of the segmented terminals 545a, 545b of the segmented-terminal set 545. FIG. 18C illustrates, in schematic end view, one embodiment of the insulation 1705 disposed between portions of the segmented terminals 545a, 545b of the segmented-terminal set 545.

In FIGS. 18A-18C, the insulation 1705 is shown disposed along the segmented-terminal set 545 such that the insulating member 1705a is disposed in the retention space 1494a between the retention member 1380 of the segmented terminal 545b and the stimulation portion 1370 of the segmented terminal 545a. Similarly, in FIGS. 18A-18C, the insulating member 1705b is shown disposed in the retention space 1494b between the retention member 1380 of the segmented terminal 545a and the stimulation portion 1370 of the segmented terminal 545b.

Figure 19A:
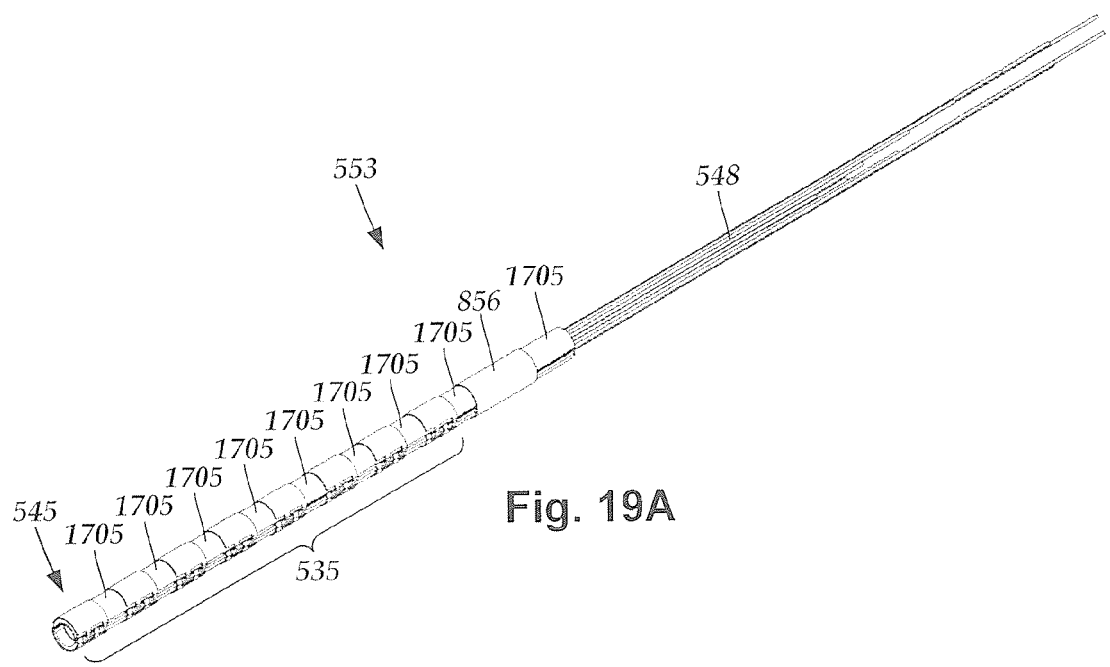
FIG. 19A is a schematic perspective view of one embodiment of the proximal portion of the lead of FIG. 11 with the insulation of FIGS. 17A-17C disposed between individual segmented terminals of the segmented-terminal sets of the terminal array of FIG. 12, according to the invention.
Figure 19B:
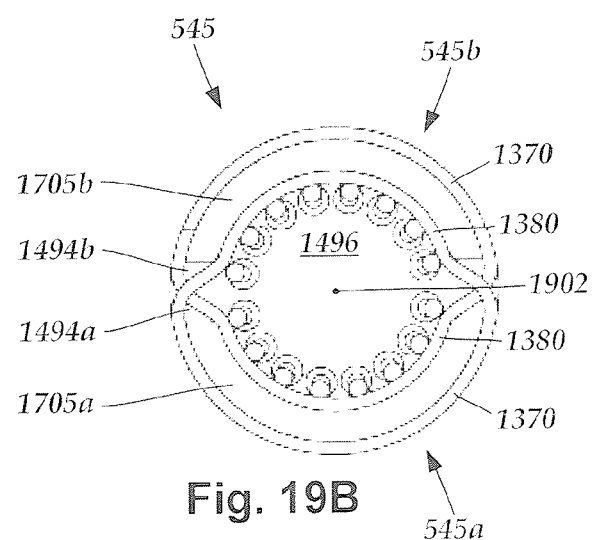
FIG. 19B is a schematic end view of one embodiment of the proximal portion of the lead of FIG. 19A, according to the invention.

Turning to FIG. 19A, in at least some embodiments the insulating members are interleaved between the segmented terminals of multiple segmented-terminal sets until all of the segmented-terminal sets of the terminal array are assembled together in a longitudinally-spaced-apart arrangement along the length of the insulating members. FIG. 19A illustrates, in schematic perspective view, one embodiment of the terminal array 535 and the insulating members 1705a, 1705b disposed along the proximal portion of the lead 553. FIG. 19B illustrates, in schematic end view, one embodiment of the terminal array 535 and the insulating members 1705a, 1705b disposed along the proximal portion of the lead 553. In at least some embodiments, the insulating members 1705a, 1705b are disposed beneath the retention sleeve 856.

As shown in FIGS. 19A-19B, in at least some embodiments the curvature of the second arced portions (1382 in FIGS. 13A-13C) (e.g., along the one or more retention members 1380) of the contacts are such that the retention member(s) 1380 of the contacts of the segmented-contact sets extend beyond a center transverse axis 1902 of the lead when the stimulation portions 1370 of the contacts are exposed along the outer surface of the lead. The center transverse axis 1902 extends longitudinally along a center of the lead. Such a design may be advantageous to facilitate placement (and retention) of the insulating members 1705a, 1705a between the connector contacts of the connector-contact sets.

In at least some embodiments, nonconductive material is disposed over the portions of the insulating material 1705a, 1705b exposed between adjacent connector-contact sets. The nonconductive material may be disposed over other exposed portions of the insulating material 1705a, 1705b including, for example, between the distal-most connector-contact set and the retention sleeve (if present), or proximal to the proximal-most connector-contact set (if applicable), or both.

The nonconductive material can be applied using any suitable technique including, for example, reflowing (heating polymer to form a molten state that oozes into available spaces and then allowing the molten material to set), overmolding, or the like or combinations thereof. In at least some embodiments, portions of the lead are ground down subsequent to application of the nonconductive material to form an isodiametric lead, or an isodiametric portion of the lead, and also to remove any nonconductive material that may be disposed over the stimulation portions of the contacts.

Figure 20:
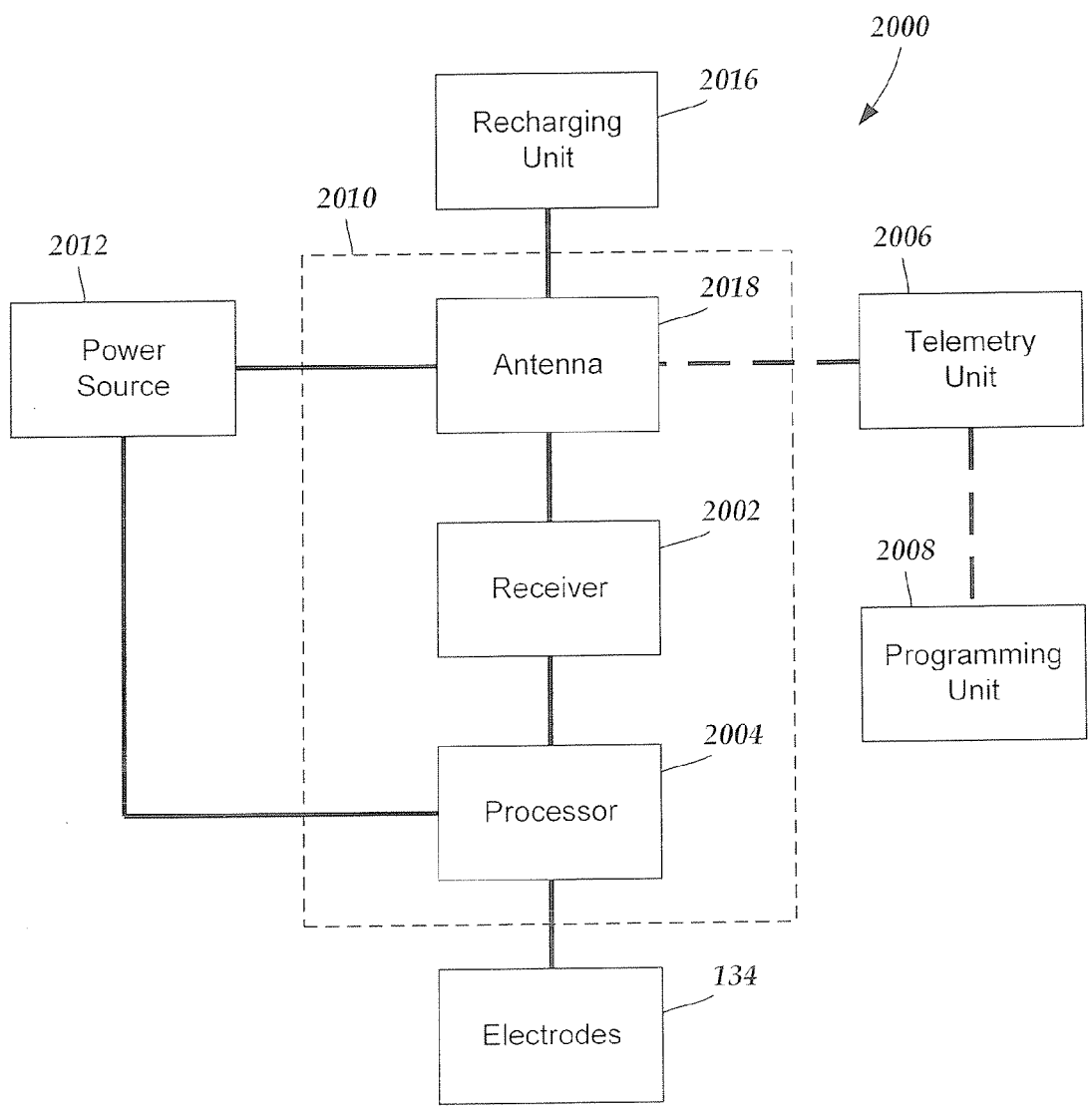
FIG. 20 is a schematic overview of one embodiment of components of an electrical stimulation system, according to the invention.

FIG. 20 is a schematic overview of one embodiment of components of an electrical stimulation system 2000 including an electronic subassembly 2010 disposed within a control module. It will be understood that the electrical stimulation system can include more, fewer, or different components and can have a variety of different configurations including those configurations disclosed in the stimulator references cited herein.

Some of the components (for example, power source 2012, antenna 2018, receiver 2002, and processor 2004) of the electrical stimulation system can be positioned on one or more circuit boards or similar carriers within a sealed housing of an implantable pulse generator, if desired. Any power source 2012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 2018 or a secondary antenna. The external power source can be in a device that is mounted on the skin of the user or in a unit that is provided near the user on a permanent or periodic basis.

If the power source 2012 is a rechargeable battery, the battery may be recharged using the optional antenna 2018, if desired. Power can be provided to the battery for recharging by inductively coupling the battery through the antenna to a recharging unit 2016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 2004 is generally included to control the timing and electrical characteristics of the electrical stimulation system. For example, the processor 2004 can, if desired, control one or more of the timing, frequency, strength, duration, and waveform of the pulses. In addition, the processor 2004 can select which electrodes can be used to provide stimulation, if desired. In some embodiments, the processor 2004 may select which electrode(s) are cathodes and which electrode(s) are anodes. In some embodiments, the processor 2004 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 2008 that, for example, allows modification of pulse characteristics. In the illustrated embodiment, the processor 2004 is coupled to a receiver 2002 which, in turn, is coupled to the optional antenna 2018. This allows the processor 2004 to receive instructions from an external source to, for example, direct the pulse characteristics and the selection of electrodes, if desired.

In one embodiment, the antenna 2018 is capable of receiving signals (e.g., RF signals) from an external telemetry unit 2006 which is programmed by a programming unit 2008. The programming unit 2008 can be external to, or part of the telemetry unit 2006. The telemetry unit 2006 can be a device that is worn on the skin of the user or can be carried by the user and can have a form similar to a pager, cellular phone, or remote control, if desired. As another alternative, the telemetry unit 2006 may not be worn or carried by the user but may only be available at a home station or at a clinician's office. The programming unit 2008 can be any unit that can provide information to the telemetry unit 2006 for transmission to the electrical stimulation system 2000. The programming unit 2008 can be part of the telemetry unit 2006 or can provide signals or information to the telemetry unit 2006 via a wireless or wired connection. One example of a suitable programming unit is a computer operated by the user or clinician to send signals to the telemetry unit 2006.

The signals sent to the processor 2004 via the antenna 2018 and receiver 2002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 2000 to cease operation, to start operation, to start charging the battery, or to stop charging the battery. In other embodiments, the stimulation system does not include an antenna 2018 or receiver 2002 and the processor 2004 operates as programmed.

Optionally, the electrical stimulation system 2000 may include a transmitter (not shown) coupled to the processor 2004 and the antenna 2018 for transmitting signals back to the telemetry unit 2006 or another unit capable of receiving the signals. For example, the electrical stimulation system 2000 may transmit signals indicating whether the electrical stimulation system 2000 is operating properly or not or indicating when the battery needs to be charged or the level of charge remaining in the battery. The processor 2004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead comprising:
   a lead body with a proximal portion, at least one distal portion, an outer surface, a circumference, and a longitudinal length;
   a plurality of contacts disposed along the lead body, the plurality of contacts comprising
      a plurality of electrodes disposed along the distal portion of the lead body, and
      a plurality of terminals disposed along the proximal portion of the lead body;
   at least one segmented-contact set formed from at least some of the plurality of contacts, the at least one segmented-contact set comprising a plurality of segmented contacts that are each at least partially disposed along a particular longitudinal position of the lead and that each extend around less than the entire circumference of the lead body and that are not in electrical contact with one another, each of the plurality of segmented-contact sets comprising a first segmented contact and a second segmented contact, the first segmented contact and the second segmented contact each comprising
      a stimulation portion having a stimulation surface exposed along the outer surface of the lead body, and
      at least one retention member coupled to the stimulation portion and disposed beneath the outer surface of the lead body,
      wherein the stimulation portion and the at least one retention member collectively form a loop of material that extends around a center transverse axis of the lead body;
   a first insulating member disposed between the stimulation portion of the first segmented contact and the at least one retention member of the second segmented contact;

a second insulating member disposed between the stimulation portion of the second segmented contact and the at least one retention member of the first segmented contact; and a plurality of lead conductors electrically coupling the plurality of electrodes to the plurality of terminals.

2. The electrical stimulation lead of claim 1 wherein, for at least one of the at least one segmented-contact set, the loop comprises a first arced portion having a first curvature and a second arced portion having a second curvature that has a different than the first curvature.

3. The electrical stimulation lead of claim 2, wherein the first arced portion is formed along the stimulation portion and the second arced portion is formed along the at least one retention member.

4. The electrical stimulation lead of claim 3, wherein the at least one retention member comprises at least one transition region having a third arced portion that has a different curvature than at least one of the first arced portion or the second arced portion.

5. The electrical stimulation lead of claim 1, wherein the at least one segmented-contact set comprises exactly two segmented contacts.

6. The electrical stimulation lead of claim 1, wherein the at least one segmented-contact set is formed entirely from electrodes of the plurality of electrodes.

7. The electrical stimulation lead of claim 1, wherein the at least one segmented-contact set is formed entirely from terminals of the plurality of terminals.

8. The electrical stimulation lead of claim 1, wherein the at least one segmented-contact set comprises a first segmented-contact set and a second segmented-contact set, wherein the first segmented-contact set is formed entirely from electrodes of the plurality of electrodes, and wherein the second segmented-contact set is formed entirely from terminals of the plurality of terminals.

9. The electrical stimulation lead of claim 1, wherein the at least one segmented-contact set comprises a plurality of segmented-contact sets, the plurality of segmented-contact sets each formed entirely from terminals of the plurality of terminals.

10. The electrical stimulation lead of claim 1, wherein the at least one segmented-contact set comprises a plurality of segmented-contact sets, and wherein each the first insulating member and the second insulating member extend beneath each of the plurality of segmented-contact sets.

11. The electrical stimulation lead of claim 1, wherein the electrical stimulation lead comprises a single proximal portion and a plurality of distal portions, the plurality of distal portions comprising a first distal portion and a second distal portion, and wherein the plurality of electrodes comprises a first electrode array disposed along the first distal portion and a second electrode array disposed along the second distal portion.

12. The electrical stimulation lead of claim 11, wherein the at least one segmented-contact set comprises a first segmented-contact set, a second segmented-contact set, and a third segmented-contact set, wherein the first segmented-contact set is formed entirely from electrodes of the first electrode array, wherein the second segmented-contact set is formed entirely from electrodes of the second electrode array, and wherein the third segmented-contact set is formed entirely from terminals of the plurality of terminals.

13. An electrical stimulation system comprising:
the electrical stimulation lead of claim 1;
a control module electrically coupleable to the plurality of electrodes of the electrical stimulation lead, the control module comprising
a housing, and
an electronic subassembly disposed in the housing; and
a connector for receiving the electrical stimulation lead, the connector comprising
a connector housing defining a port configured and arranged for receiving the proximal portion of the lead body of the electrical stimulation lead, and
a plurality of connector contacts disposed in the connector housing, the plurality of connector contacts configured and arranged to couple to the plurality of terminals of the electrical stimulation lead when the proximal portion of the lead body of the electrical stimulation lead is received by the port.

14. The electrical stimulation system of claim 13, wherein the plurality of connector contacts comprises a plurality of segmented connector contacts, and wherein the electrical stimulation system further comprises an alignment assembly configured and arranged for aligning the first and second segmented contacts of the at least one segmented-contact sets circumferentially with the plurality of segmented connector contacts.

15. A method of forming the electrical stimulation lead of claim 1, the method comprising:
attaching a first conductor of the plurality of lead conductors to the first segmented contact of the at least one segmented-contact set;
attaching a second conductor of the plurality of lead conductors to the second segmented contact of the at least one segmented-contact set;
arranging the first segmented contact and the second segmented contact into the first segmented-contact set with the stimulation portion of the first segmented contact disposed opposite the stimulation portion of the second segmented contact and with the at least one retention member of the first segmented contact facing the at least one retention member of the second segmented contact to form a first retention space defined between the stimulation portion of the first segmented contact and the at least one retention member of the second segmented contact and a second retention space defined between the stimulation portion of the second segmented contact and the at least one retention member of the first segmented contact;
extending the first insulating member through the first retention space of the first segmented-contact set;
extending the second insulating member through the second retention space of the first segmented-contact set;
attaching the first conductor to a first electrode of the plurality of electrodes disposed along the distal portion of the lead body or a first terminal of the plurality of terminals disposed along the proximal portion of the lead body; and
attaching the second conductor to one of a second electrode of the plurality of electrodes disposed along the distal portion of the lead body or a second terminal of the plurality of terminals disposed along the proximal portion of the lead body.

16. The method of claim 15, wherein arranging the first segmented contact and the second segmented contact into the first segmented-contact set comprises arranging a first segmented terminal of the plurality of terminals and a second segmented terminal of the plurality of terminals into a first segmented-terminal set along the proximal portion of the lead body.

17. The method of claim 16, further comprising arranging a third segmented terminal of the plurality of terminals and a fourth segmented terminal of the plurality of terminals into a second segmented-terminal set disposed along the proximal portion of the lead body and longitudinally displaced from the first segmented-terminal set.

18. The method of claim 16, further comprising extending the first insulating member through a third retention space defined along the second segmented-contact set.

19. The method of claim 16, further comprising extending the second insulating member through a fourth retention space defined along the second segmented-contact set.

20. The method of claim 15, wherein arranging the first segmented contact and the second segmented contact into the first segmented-contact set comprises arranging a first segmented electrode of the plurality of electrodes and a second segmented electrode of the plurality of electrodes into a first segmented-electrode set disposed along the at least one distal portion of the lead body.

\* \* \* \* \*